US010999986B2

(12) United States Patent
Jena et al.

(10) Patent No.: US 10,999,986 B2
(45) Date of Patent: May 11, 2021

(54) INCREASING HYBRID SEED PRODUCTION THROUGH HIGHER OUTCROSSING RATE IN CYTOPLASMIC MALE STERILE RICE AND RELATED MATERIALS AND METHODS

(71) Applicant: International Rice Research Institute, Los Baños (PH)

(72) Inventors: Kshirod K. Jena, Cuttack (IN); Balram Marathi, Hyderabad (IN); Joie Ramos, Los Baños (PH); Reynaldo Diocton, IV, Samar (PH); Ricky Vinarao, Los Baños (PH); G. D. Prahalada, Sira (IN); Sung-Ryul Kim, Ulsan (KR)

(73) Assignee: International Rice Research Institute, Los Baños (PH)

( * ) Notice: Subject to any disclaimer, the term of this patent is extended or adjusted under 35 U.S.C. 154(b) by 12 days.

(21) Appl. No.: 15/579,247

(22) PCT Filed: Jun. 5, 2016

(86) PCT No.: PCT/IB2016/053294
§ 371 (c)(1),
(2) Date: Dec. 4, 2017

(87) PCT Pub. No.: WO2016/193953
PCT Pub. Date: Dec. 8, 2016

(65) Prior Publication Data
US 2018/0160638 A1 Jun. 14, 2018

Related U.S. Application Data

(60) Provisional application No. 62/171,524, filed on Jun. 5, 2015.

(51) Int. Cl.
*A01H 1/04* (2006.01)
*C12Q 1/6895* (2018.01)
*A01H 5/10* (2018.01)
*A01H 1/02* (2006.01)
*A01H 4/00* (2006.01)
*C12N 15/82* (2006.01)

(52) U.S. Cl.
CPC .............. *A01H 1/04* (2013.01); *A01H 1/02* (2013.01); *A01H 4/008* (2013.01); *A01H 5/10* (2013.01); *C12Q 1/6895* (2013.01); *C12N 15/8289* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 4,764,643 A | 8/1988 | Calub |
| 2012/0240285 A1 | 9/2012 | Jinushi et al. |

FOREIGN PATENT DOCUMENTS

| CN | 102333439 | 1/2012 |
| WO | WO 2016/193953 | 12/2016 |
| WO | WO 2018/224861 | 12/2018 |

OTHER PUBLICATIONS

Miles et al (2008, "Quantitative Trait Locus (QTL) Analysis", Nature Education 1(1):208).*
Taillebois et al (1986, "Improving Outcrossing Rate in Rice (*Oryza sativa* L.)", Proceedings of the International Symposium on Hybrid Rice, pp. 175-180).*
Miles et al (2008, "Quantitative Trait Locus (QTL) Analysis", Nature Education 1(1):208; p. 4, 2nd paragraph).*
(Taillebois et al 1986, Proceedings of the International Symposium on Hybrid Rice, pp. 175-180).*
Communication Pursuant to Article 94(3) EPC dated Jan. 18, 2019 From the European Patent Office Re. Application No. 16729639.1. (4 Pages).
Examination Report dated Feb. 5, 2018 From the Ministry of Science and Technology of the Socialist Republic of Vietnam Re. Application No. 1-2018-00038 and Its Summary in English. (2 pages).
International Preliminary Report on Patentability dated Dec. 14, 2017 From the International Bureau of WIPO Re. Application No. PCT/IB2016/053294. (7 Pages).
International Search Report and the Written Opinion dated Dec. 1, 2017 From the International Searching Authority Re. Application No. PCT/IB2017/053363. (16 Pages).
International Search Report and the Written Opinion dated Aug. 8, 2016 From the International Searching Authority Re. Application No. PCT/IB2016/053294.
Angeles-Shim et al. "Molecular Analysis of *Oryza latifolia* Desv. (CCDD Genome)-Derived Introgression Lines and Identification of Value-Added Traits for Rice (*O. sativa* L.) Improvement", The Journal of Heredity, 105(5): 676-689, Advance Access Published Jun. 17, 2014.
Causse et al. "Prospective Use of *Oryza longistaminata* for Rice Breeding", Rice Genetics II—Proceedings of the Second International Rice Genetics Symposium, IRRI, Manila, Philippines,May 14-18, 1990, XP002760153, p. 81-89, May 14, 1990. p. 87, Para.2.
Dayun et al. "Preliminary Report on Transfer Traits of Vegetative Propagation From Wild Rice species to *Oryza sativa* Via Distant Hybridization and Embryo Rescue", The Kasetsart Journal Natural Sciences, 34(1): 1-11, Jan.-Mar. 2000.
Endo et al. "Molecular Breeding of A Novel Herbicide-Tolerant Rice by Gene Targeting", The Plant Journal, 52(1): 157-166, Oct. 2007.

(Continued)

*Primary Examiner* — Stuart F Baum

(57) ABSTRACT

Methods for increasing hybrid seed production are provided. Increased hybrid seed production is achieved through higher outcrossing rates in cytoplasmic male sterile (CMS) lines of rice by introgressing the long stigma trait of *Oryza longistaminata*. CMS lines having higher outcrossing rates capable of high hybrid seed set are also provided.

Figure 1:
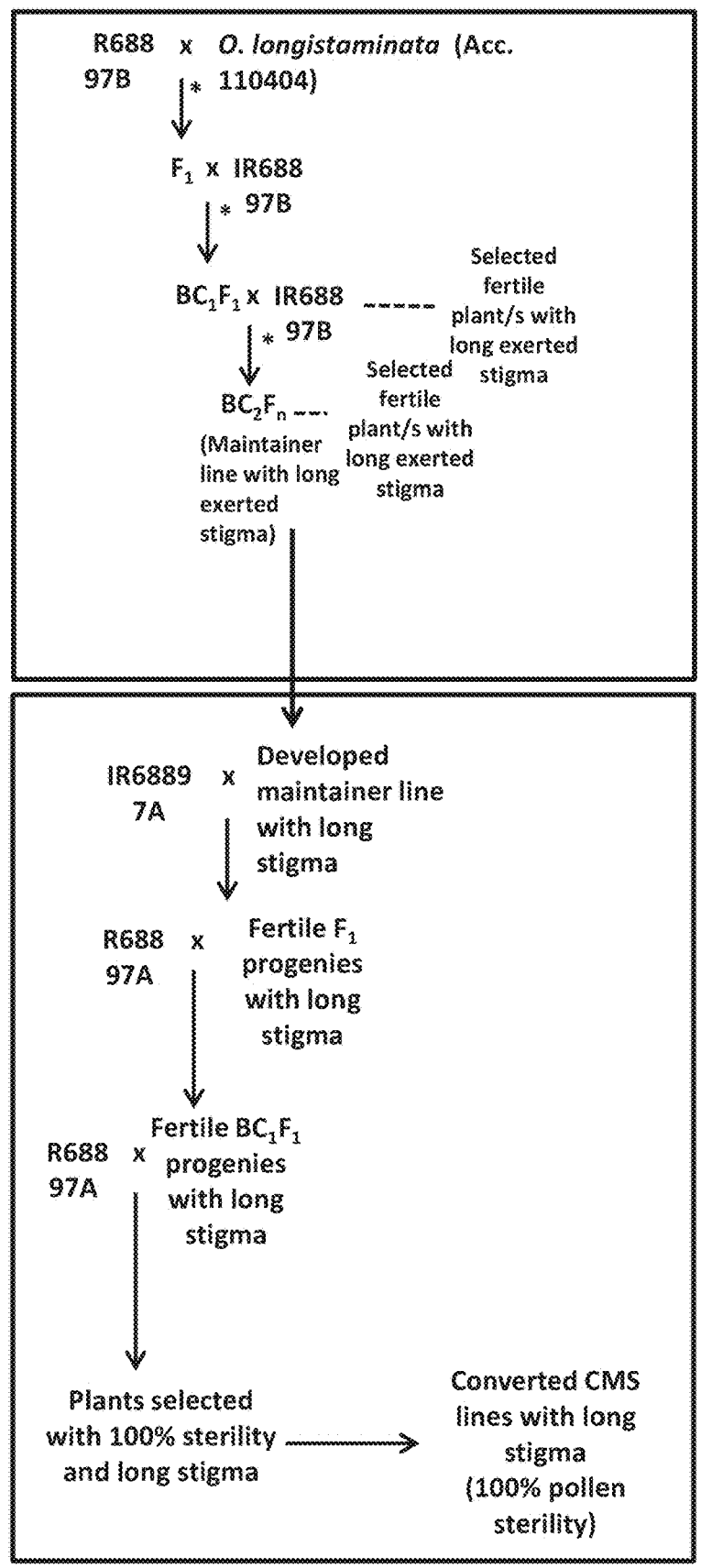

8 Claims, 17 Drawing Sheets
(15 of 17 Drawing Sheet(s) Filed in Color)

Specification includes a Sequence Listing.

(56) References Cited

OTHER PUBLICATIONS

IRRI "Rice Genetics II", International Rice Research Institute, IRRI, Proceedings of the Second International Rice Genetics Symposium, Manila, Philippines, May 14-18, 1990, p. 1-844, 1991.
Janila et al. "Enhanced Resistance to Foliar Fungal Diseases and Improved Oil Quality in Peanut Using MABC Approach", ICRISAT, Internatioanl Crops Research Institute for the Semi-Arid Topics, CEG, Center of the Excellence in Genomics, Striving Towards Efficient Breeding and Research, 5th International Conference on Next Generation Genomics & Integrated Breeding for Crop Improvement, Patancheru, India, Feb. 18-20, 2015, Poster Presentation Abstracts, p. 162, # NGG-P52, Feb. 18, 2015.
Liu et al. "Fine Mapping and Cadidate Gene Analysis of qSTL3, A Stigma Length-Conditioning Locus in Rice (*Oryza sativa* L.)", PLOS ONE, XP055425946, 10(6): e127938-1-e0127938-15, Jun. 1, 2015.
Marathi et al. "Floral Traits to Enhance Outcrossing for Higher Hybrid Seed Production in Rice: Present Status and Future Prospects", Euphytica, XP35409378, 201(1): 1-14, Sep. 14, 2014. p. 2, r-h col., Para 2-p. 3, r-h col., Last Para.
Marathi et al. "SNP Genotyping and Characterization of Pistil Traits Revealing a Distinct Phylogenetic Relationship Among the Species of *Oryza*", Euphytica, XP035409386, 201(1): 131-148, Published Online Jul. 25, 2014.
Okuzaki et al. "A Novel Mutated Acetolactate Synthase Gene Conferring Specific Resistance to Pyrimidinyl Carboxy Herbicides in Rice", Plant Molecular Biology, 64(1-2): 219-224, Published Online Mar. 3, 2007.
Ramos et al. "Development of Chromosome Segment Substitution Lines ( CSSLs) of *Oryza longistaminata* A. Chev. & Röhr in the Background of the Elite Japonica Rice Cultivar, Taichung 65 and Their Evaluation for Yield Traits", Euphytica, XP035991348, 210(2): 151-163, Apr. 2, 2016. Abstract, Fig.2.
Sheeba et al. "Genetic Variability for Floral Traits Influencing Outcrossing in the CMS Lines of Rice", Indian Journal of Agricultural Research, 40(4): 272-276, 2006.
Taillebois et al. "Improving Outcrossing Rate in Rice (*Oryza sativa* L.)", Hybrid Rice—Proceedings of the International Symposium on Hybrid Rice, IRRI, Changsha, Hunan, China, Oct. 6-10, 1986, XP002760152, p. 175-180, Oct. 6, 1988. p. 179.
Search Report and Opinion dated Jan. 13, 2020 From the Servico Publico Federal, Ministerio da Economia, Instituto Nacional da Propriedade Industrial do Brasil Re. Application No. BR112017026243-6 and Its Translation Into English. (6 Pages).
International Preliminary Report on Patentability dated Dec. 19, 2019 From the International Bureau of WIPO Re. Application No. PCT/IB2017/053363. (8 Pages).
Notification of Office Action and Search Report dated Dec. 18, 2019 From the State Intellectual Property Office of the People's Republic of China Re. Application No. 201680033206.1. (6 Pages).
Translation dated Dec. 31, 2019 of Notification of Office Action and Search Report dated Dec. 18, 2019 From the State Intellectual Property Office of the People's Republic of China Re. Application No. 201680033206.1. (9 Pages).
Examination Report dated Oct. 16, 2020 From the Kementeriaan Hukum Dan Hak Asasi Manusia, Republik Indonesia, Direktorat Jenderal Kekayaan Intelektual [Ministry of Law and Human Rights, Republic of Indonesia, General Directorate of Intellectual Property] Re. Application No. PID201709844 and Its Machine Translation Into English. (4 Pages).

* cited by examiner

Converted CMS x Restorer
lines               Line
(IR127841A &    (IR71604-4-1-4-4-4-2-
IR127842A)         2-2R)

Out-crossing Rate

Experimental Lay-out:

| Restorer (Pollinator) | Restorer | Restorer | Restorer | Restorer | Restorer | Restorer |
|---|---|---|---|---|---|---|
| | | | R1-OCF15-91 | | | |
| | | | R2-OCF15-91 | | | |
| | | | Restorer | | | |
| | | | R1-OCF15-107 | | | |
| | | | R2-OCF15-107 | | | |
| | | | Restorer | | | |
| | | | R1-OCF15-108 | | | |
| | | | R2-OCF15-108 | | | |
| | | | Restorer | | | |
| | | | R1-OCF15-111 | | | |
| | | | R2-OCF15-111 | | | |
| | | | Restorer | | | |
| | | | R1-IR68897A | | | |
| | | | R2-IR68897A | | | |
| | | | Restorer | | | |
| | | | R1-IR58025A | | | |
| | | | R2-IR58025A | | | |
| | | | Restorer | | | |

FIG. 2

| Lines | Stigma Brush | Stigma Non-Brush | Stigma | Stigma width |
|---|---|---|---|---|
| IR68897A | 1.58 | 0.842 | 2.43 | 0.547 |
| OCF15-107-1 | 2.53* | 0.698 | 3.23* | 0.651 |
| OCF15-107-2 | 2.41* | 0.689 | 3.10* | 0.696 |
| OCF15-107-4 | 2.37* | 0.809 | 3.18* | 0.664 |
| OCF15-107-5 | 2.76* | 0.794 | 3.55* | 0.632 |
| OCF15-107-6 | 2.35* | 0.842 | 3.19* | 0.575 |
| OCF15-107-7 | 2.44* | 0.694 | 3.13* | 0.680 |
| OCF15-107-8 | 2.91* | 0.942 | 3.85* | 0.719* |
| OCF15-107-9 | 2.54* | 0.787 | 3.33* | 0.654 |
| OCF15-107-10 | 2.67* | 0.890 | 3.56* | 0.654 |
| OCF15-107-11 | 2.64* | 0.741 | 3.38* | 0.796* |
| OCF15-107-12 | 2.55* | 0.808 | 3.36* | 0.658 |
| OCF15-107-13 | 2.22* | 0.780 | 3.00* | 0.678 |
| OCF15-107-14 | 2.51* | 0.852 | 3.36* | 0.676 |
| OCF15-107-15 | 2.25* | 0.828 | 3.08* | 0.691 |
| OCF15-107-16 | 2.25* | 0.692 | 2.94 | 0.723* |
| OCF15-107-17 | 2.69* | 0.735 | 3.42* | 0.715* |

FIG. 5

| Seed Set (%) | | | | | | | | | | |
|---|---|---|---|---|---|---|---|---|---|---|
| Line | Day 1 | Day 2 | Day 3 | Day 4 | Day 5 | Day 6 | Day 7 | Day 8 | Day 9 | Day 10 |
| IR68897A | 64.20 | 39.71 | 42.21 | 38.21 | 4.49 | 0.00 | 0.00 | 0.00 | 0.00 | 0.00 |
| OCF15-2 | 45.59 | 28.38 | 60.48 | 16.67 | 41.67 | 10.96 | 8.77 | 0.00 | 0.00 | 0.00 |
| OCF15-17 | 56.10 | 46.03 | 63.74 | 33.66 | 5.36 | 31.82 | 1.92 | 0.00 | 0.00 | 0.00 |
| OCF15-22 | 66.05 | 30.26 | 21.21 | 42.25 | 1.99 | 3.23 | 0.00 | 0.00 | 0.00 | 0.00 |
| OCF15-40 | 47.25 | 17.71 | 14.29 | 46.20 | 5.22 | 8.33 | 0.00 | 0.00 | 0.00 | 0.00 |

| Lines | Pollen Fertility (%) | Send Set (%) |
|---|---|---|
| IR68897A | 0 | 18 |
| OCF15-107-3 | 0 | 62 |
| OCF15-107-3 | 0 | 64 |
| OCF15-107-9 | 0 | 67 |

| Entry | StigmaBrush | StigmaNon-brush | Stigma | StigmaBreadth | Max%SeedSet |
|---|---|---|---|---|---|
| OCF15-107 | 2.37 | 0.70 | 3.07 | 0.72 | 69.9 |
| OCF15-107 | 2.54 | 0.67 | 3.21 | 0.67 | 68.0 |
| OCF15-107 | 2.11 | 0.63 | 2.74 | 0.72 | 66.9 |
| OCF15-107 | 2.59 | 1.02 | 3.61 | 0.62 | 65.3 |
| OCF15-107 | 2.73 | 0.69 | 3.41 | 0.62 | 63.5 |
| OCF15-108 | 2.32 | 0.64 | 2.96 | 0.62 | 80.5 |
| OCF15-108 | 2.84 | 0.79 | 3.63 | 0.68 | 74.4 |
| OCF15-108 | 2.38 | 0.68 | 3.06 | 0.70 | 73.3 |
| OCF15-108 | 2.86 | 0.77 | 3.63 | 0.73 | 68.5 |
| OCF15-108 | 2.67 | 0.72 | 3.40 | 0.73 | 66.9 |
| OCF15-108 | 2.43 | 0.78 | 3.21 | 0.65 | 65.8 |
| IR68897A | 1.57 | 0.79 | 2.36 | 0.56 | 5 - 20 |

FIG. 8

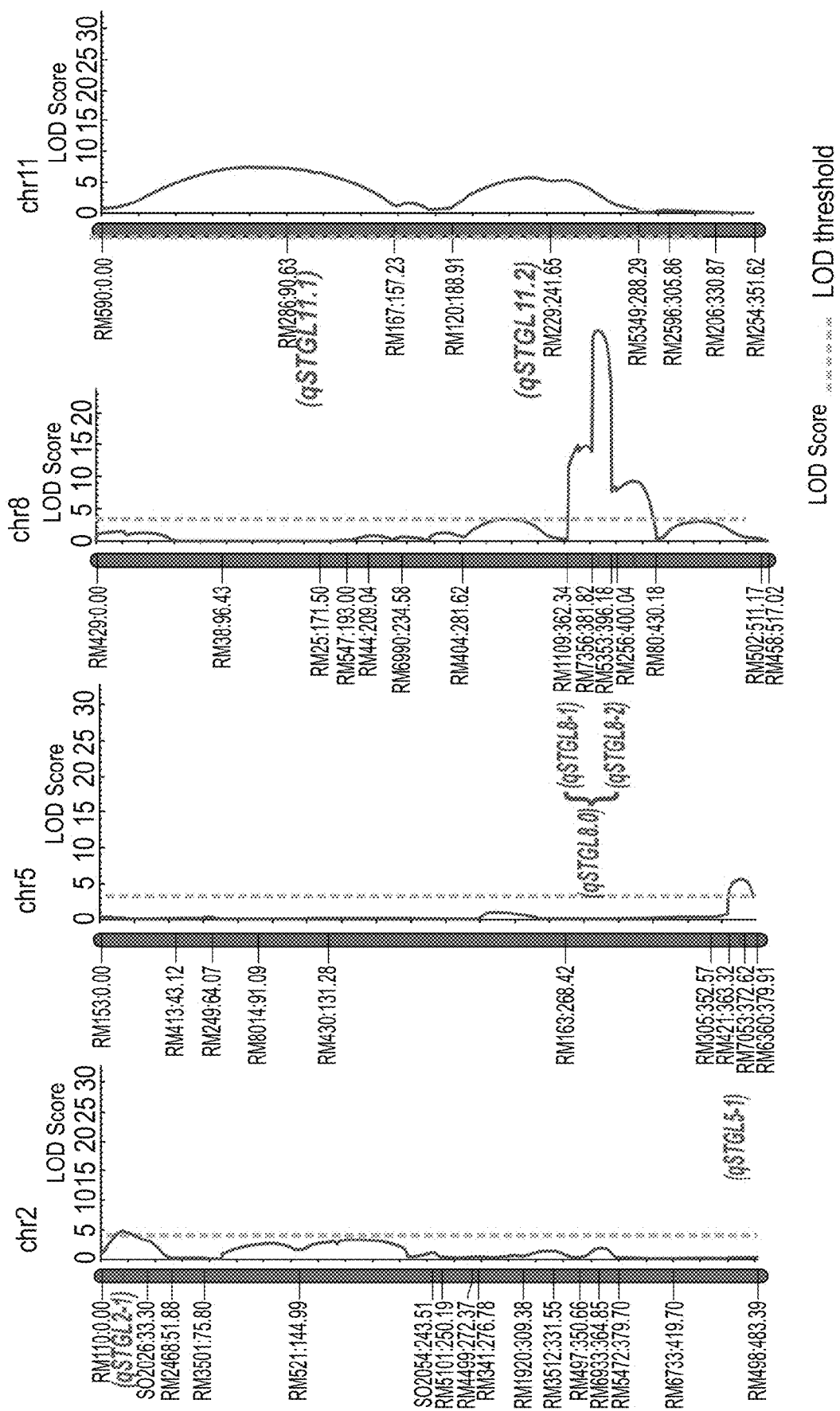
FIG. 9A  Diagram showing the linkage map of major QTLs identified for stigma length (qSTGL2-1, qSTGL5-1, qSTGL8-1, qSTGL8-2, qSTGL11-1 and qSTGL11-2) by composite interval mapping

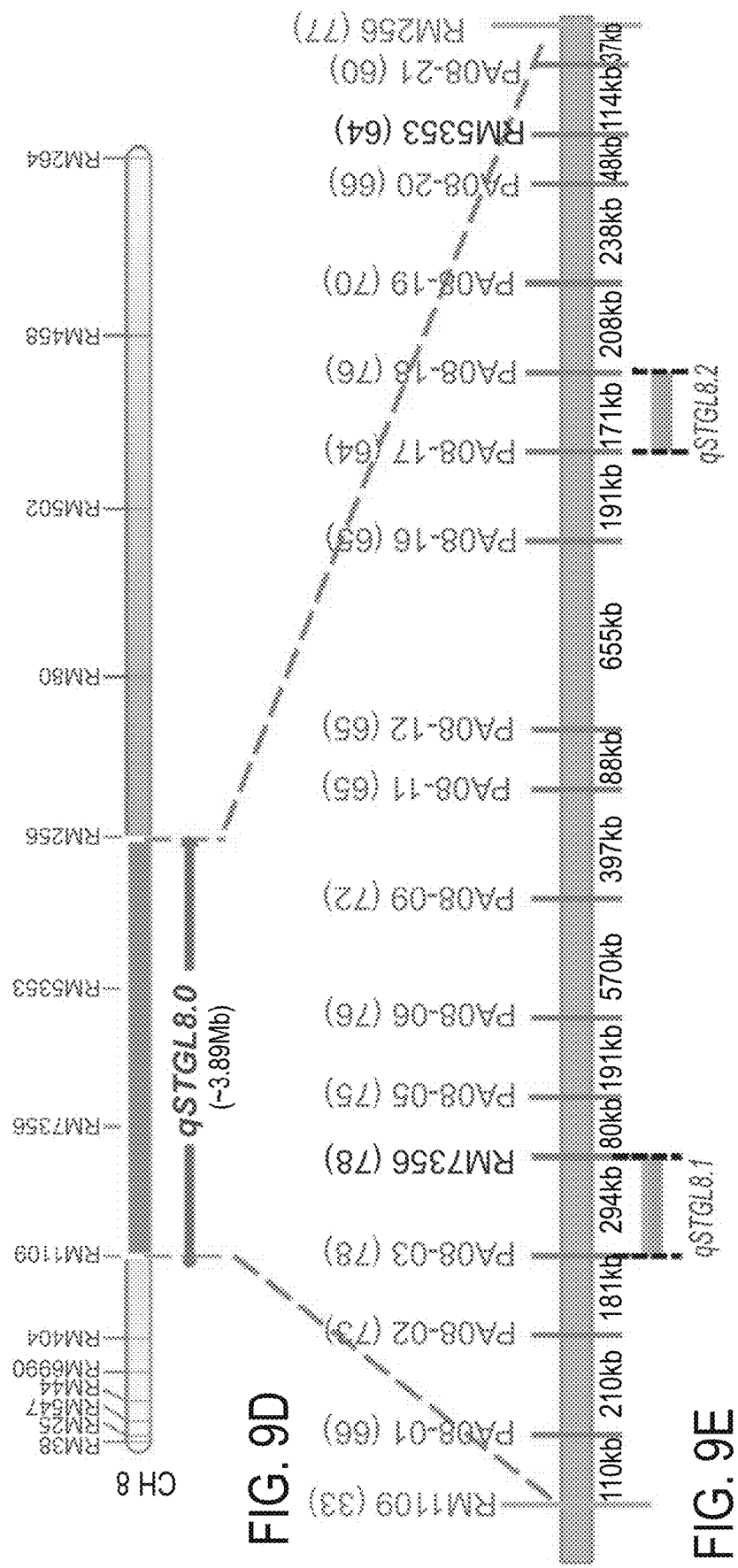

FIG. 9G

| GENOTYPE | PHENOTYPE |
|---|---|
| B | Long Stigma |
| B | Long Stigma |
| H | Long Stigma |
| A | Long Stigma |
| H | Long Stigma |
| A | Short Stigma |
| H | Long Stigma |
| B | Long Stigma |
| B | Long Stigma |
| B | Long Stigma |
| H | Long Stigma |
| H | Long Stigma |
| H | Long Stigma |
| H | Long Stigma |
| A | Short Stigma |
| B | Long Stigma |

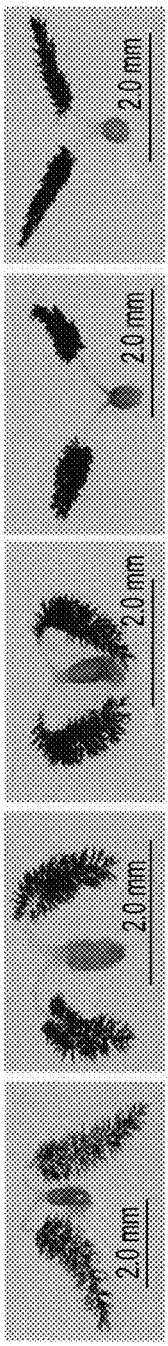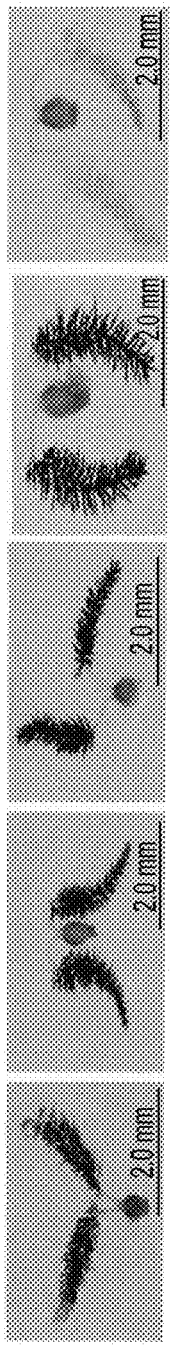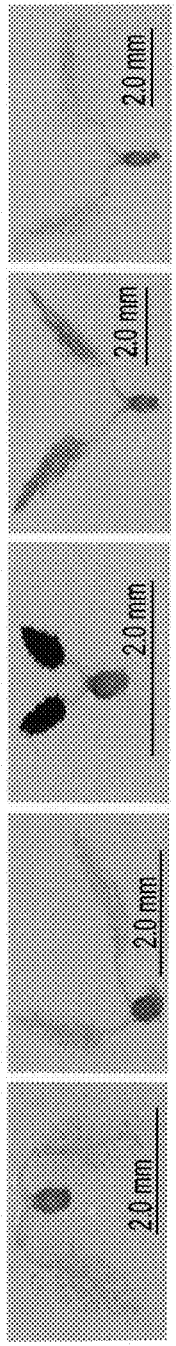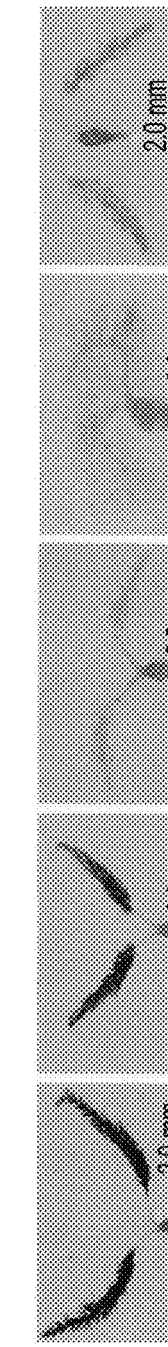

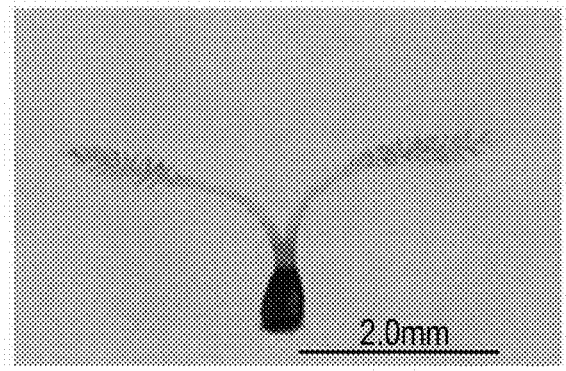
IR68897B (No stigma exsertion)
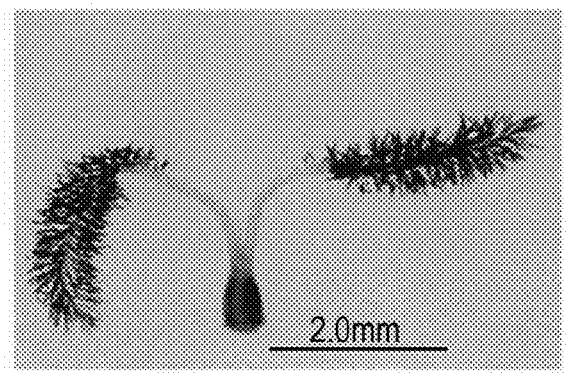
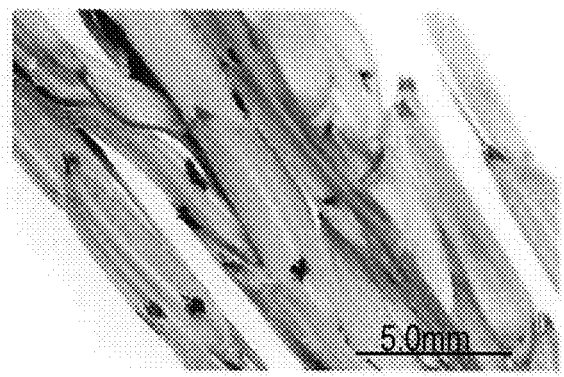
Stigma exsertion in IR68897B_Improved
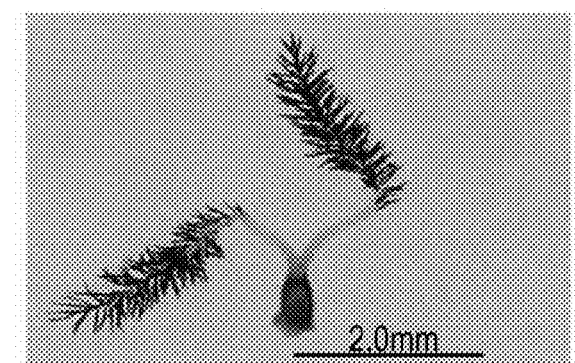
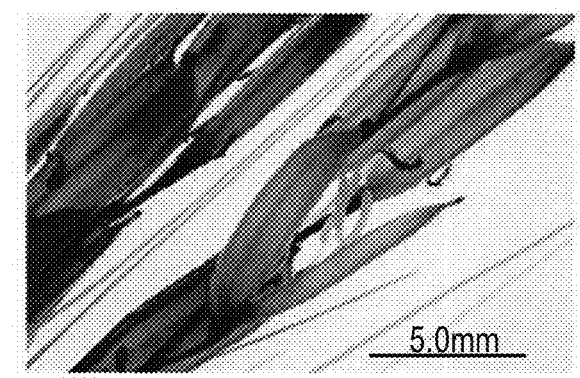
Stigma exsertion in IR68897A testcross
FIG. 11

INCREASING HYBRID SEED PRODUCTION THROUGH HIGHER OUTCROSSING RATE IN CYTOPLASMIC MALE STERILE RICE AND RELATED MATERIALS AND METHODS

RELATED APPLICATIONS

This application is a National Phase of PCT Patent Application No. PCT/IB2016/053294 having International filing date of Jun. 5, 2016, which claims the benefit of priority under 35 USC § 119(e) of U.S. Provisional Patent Application No. 62/171,524 filed on Jun. 5, 2015. The contents of the above applications are all incorporated by reference as if fully set forth herein in their entirety.

SEQUENCE LISTING STATEMENT

The ASCII file, entitled 71769SequenceListing.txt, created on Dec. 4, 2017, comprising 12,045 bytes, submitted concurrently with the filing of this application is incorporated herein by reference. The sequence listing submitted herewith is identical to the sequence listing forming part of the international application.

BACKGROUND OF THE INVENTION

Rice is the staple food of more than half the world's population, providing more than 20% of the daily caloric intake of over 3.5 billion people. It is estimated that an additional 116 million tons of rice will be needed by 2035 to feed the world's growing population.

Beginning in the 1940s and 1950s, increasing yields progressively replaced area expansion as the principal source of growth in world grain production. The Green Revolution occurring between the 1940s and late 1960s saw the development of new agricultural practices and technologies that significantly improved grain yield per acre, and is credited with saving millions from mass famine in India during the early 1960s. In particular, the rice variety IR8 was developed, which produced more grain per plant when grown with irrigation and fertilizers. Many additional high-yielding rice lines have been developed since IR8.

Green Revolution technologies, which spurred gains in annual rice yields of more than 3% are now generally considered almost exhausted of any further productivity gains, with annual yield gains falling to around 1.25% since 1990. Decreases in annual gains have lead to plateaus in rice yield in many small to medium-sized countries, including Japan and South Korea. Rice yields in larger countries such as India and China appear to be approaching their own glass ceilings.

Beginning in the early 1970s, significant research efforts have gone into developing hybrid rice, which has been shown to have yields of up to 20% greater than those of conventional Green Revolution high-yielding lines. It was during the early 1970s that Chinese researchers discovered a wild-abortive cytoplasmic male sterile (WA-CMS) rice plant on Hainan Island. This discovery led to development of three-line hybrid rice breeding in China, where hybrid rice has been grown commercially since 1976. This led to Chinese hybrid rice yield surpassing 6.0 t ha$^{-1}$.

Although hybrid rice has been commercialized on a large scale, particularly in China where hybrid rice covers more than 50% of the total rice-planted area and accounts for about two-thirds of the national production, transferring Chinese hybrid technology to other Asia countries has proven difficult. For hybrid rice commercialization to be successful, hybrid rice seeds must be affordable for farmers, as fresh hybrid seeds are required each season.

Cultivated rice is predominantly self-fertilizing due to the morphology of its flower, i.e., the anthers and stigma are shorter, and pollen is released shortly after the florets open. Outcrossing rates in cultivated rice varieties have diminished along with changes in the morphology of rice flowers during the process of domestication, giving outcrossing rates of about 0.01%. The low rate of outcrossing causes poor hybrid seed production (seed set of 5-20%), resulting in high costs for hybrid rice seeds. These two factors have been cited as major constraints for extending hybrid rice.

It would be beneficial to develop rice varieties and lines with improved outcrossing rates useful for increasing hybrid seed production.

ADDITIONAL BACKGROUND ART

Marathi et al. 2014 Euphytica doi:10.1007/s10681-014-1213-2;
Sheeba et al. 2006 Indian J. Agric. Res. 40(4):272-276;
Liu et al. 2015 PLOS ONE I DOI:10.1371.

SUMMARY OF THE INVENTION

A cultivated rice plant comprising an introgression including at least one *Oryza longistaminata* quantitative trait locus (QTL) associated with stigma length, the cultivated rice plant having an out-crossing rate of at least 60%.

According to an aspect of some embodiments of the present invention there is provided a cultivated rice plant comprising an introgression including at least one *Oryza longistaminata* quantitative trait locus (QTL) associated with stigma length, the cultivated rice plant having an out-crossing rate of at least 50%, 55%, 60%, 65%, 70%, 80%, 85%, 90% or more.

According to a specific embodiment, the rice plant has an out-crossing rate of at least 60%.

According to an aspect of some embodiments of the present invention there is provided a cultivated rice plant comprising an introgression including at least one *Oryza longistaminata* quantitative trait locus (QTL) associated with stigma length selected from the group consisting of: qSTGL8-1 and qSTGL8-2.

According to some embodiments of the invention, the rice plant is a cytoplasmic male sterile line.

According to some embodiments of the invention, the rice plant is a maintainer line.

According to some embodiments of the invention, the rice plant has an out-crossing rate of at least 50%, 55%, 60%, 65%, 70%, 80%, 85%, 90% or more.

According to a specific embodiment, the rice plant has an out-crossing rate of at least 60%.

According to some embodiments of the invention, the rice plant comprises at least an additional introgression including at least one *Oryza longistaminata* QTL associated with stigma length, stigma area, style length, stigma breadth or total pistil length.

According to some embodiments of the invention, the at least one *Oryza longistaminata* QTL associated with stigma length, stigma area, style length, stigma breadth and pistil length is selected from the group consisting of qSTGL2-1, qSTGL5-1, qSTGL11-1, qSTGL11-2; qSTGA8-2; qSTYL1-1, qSTYL5-2, qSTYL8-1; qSTGB1-1, qSTGB3-1; qPSTL1-1, qPSTL1-3 and qPSTL11-1.

According to some embodiments of the invention, a marker of the at least one additional QTL is selected from the group consisting of stigma length, RM110 (qSTGL2-1), RM421 (qSTGL5-1), RM7356 (qSTGL8-1), RM5353 (qSTGL8-1), RM256 (qSTGL8-2), RM80 (qSTGL8-2), RM590 (qSTGL11-1), RM286 (qSTGL11-1), RM120 (qSTGL11-2); RM229 (qSTGL11-2); stigma area, RM80 (qSTGA8-2); style length, RM319 (qSTYL1-1), RM7653 (qSTYL5-2), RM404 (qSTYL8-1); stigma breadth, RM403 (qSTGB1-1), RM3525 (qSTGB3-1); and pistil length, RM3604 (qPSTL1-1); RM3640 (qPSTL1-3); and RM5997 (qPSTL11-1).

According to some embodiments of the invention, at least one marker for the QTL associated with stigma length is selected from the group consisting of PA08-03, RM7356, PA08-17 and PA08-18.

According to some embodiments of the invention, the introgression comprising QTL associated with stigma length is positioned between markers PA08-03 to RM7356 or PA08-17 to PA08-18.

According to some embodiments of the invention, the rice plant is of a line selected from the group consisting of IR68897A, IR58025A, IR127841A and IR127842A.

According to an aspect of some embodiments of the present invention there is provided a hybrid rice plant having the rice plant as a parent or an ancestor.

According to an aspect of some embodiments of the present invention there is provided a processed product comprising DNA of the rice plant.

According to some embodiments of the invention, the processed product is selected from the group consisting of food, feed, construction material and paper products.

According to some embodiments of the invention, the processed product is meal.

According to an aspect of some embodiments of the present invention there is provided an ovule of the rice plant.

According to an aspect of some embodiments of the present invention there is provided a protoplast produced from the rice plant.

According to an aspect of some embodiments of the present invention there is provided a tissue culture produced from protoplasts or cells from the rice plant, wherein the protoplasts or cells of the tissue culture are produced from a plant part selected from the group consisting of: leaves; pollen; embryos; cotyledon; hypocotyls; meristematic cells; roots; root tips; pistils; anthers; flowers; stems; glumes; and panicles.

According to an aspect of some embodiments of the present invention there is provided a rice plant regenerated from the tissue culture, wherein the rice plant is a cytoplasmic male sterile rice plant having all the morphological and physiological characteristics of the rice plant.

According to some embodiments of the invention, a long stigma trait of Oryza longistaminata is detected in the rice plant by detecting at least one marker for at least one Oryza longistaminata quantitative trait locus associated with stigma length and/or associated with total stigma and style length.

According to some embodiments of the invention, the at least one marker for the at least one Oryza longistaminata quantitative trait locus associated with stigma length is selected from the group consisting of: RM110 (qSTGL2-1), RM421 (qSTGL5-1), RM7356 (qSTGL8-1), RM5353 (qSTGL8-1), RM256 (qSTGL8-2), RM80 (qSTGL8-2), RM590 (qSTGL11-1), RM286 (qSTGL11-1), RM120 (qSTGL11-2) and RM229 (qSTGL11-2).

According to some embodiments of the invention, the at least one Oryza longistaminata quantitative trait locus associated with total stigma and style length is selected from the group consisting of: qPSTL1-1, qPSTL1-3, and qPSTL11-1.

According to some embodiments of the invention, the at least one marker for the at least one Oryza longistaminata quantitative trait locus associated with total stigma and style length is selected from the group consisting of: RM3604 (qPSTL1-1); RM3746 (qPSTL1-1); RM3640 (qPSTL1-3); RM8134 (qPSTL1-3); and RM5997 (qPSTL11-1); RM254 (qPSTL11-1).

According to an aspect of some embodiments of the present invention there is provided a method of producing a cytoplasmic male sterile rice plant comprising a long stigma trait of Oryza longistaminata, the method comprising crossing a rice plant of a stable cytoplasmic male sterile line with a rice plant of a suitable maintainer line, wherein the suitable maintainer line is a fertile rice line complementary to the cytoplasmic male sterile line, and wherein the rice plant of the maintainer line comprising an introgression including at least one Oryza longistaminata quantitative trait locus (QTL) associated with stigma length selected from the group consisting of: qSTGL8-1 and qSTGL8-2.

According to some embodiments of the invention, the long stigma trait of Oryza longistaminata is introgressed into a rice plant of the maintainer line by a method comprising the steps of:

crossing a rice plant of the maintainer line with a rice plant of Oryza longistaminata to produce one or more $F_1$ progeny rice plants;

backcrossing an $F_1$ progeny rice plant with a rice plant of the maintainer line to produce one or more $BC_1F_1$ progeny rice plants, and selecting one or more fertile $BC_1F_1$ plants increased stigma length relative to rice plants of the maintainer line;

backcrossing the selected progeny of step b) with a rice plant of the maintainer line;

selecting one or more fertile progeny rice plants produced from the backcross of step c) having all of the physiological and morphological characteristics of the maintainer line, except for increased stigma length; and intercrossing or selfing the one or more rice plants selected in step d) one or more times to produce one or more progeny rice plants of $F_2$ or later generations.

According to some embodiments of the invention, step c) is carried out 1 to 5 time to produce $BC_2F_1$ to $BC_6F_1$ progeny rice plants.

According to some embodiments of the invention, the maintainer line is of germplasm accession IRGC 110404.

According to some embodiments of the invention, progeny rice plants are produced in steps a), b) and c) by embryo rescue.

According to some embodiments of the invention, the method further comprises the steps of:

selecting one or more fertile progeny rice plants produced by the method as described herein having increased stigma length relative to rice plants of the maintainer line not introgressed with the long stigma trait of Oryza longistaminata;

backcrossing the one or more progeny rice plants selected in step a) with a rice plant from the stable cytoplasmic male sterile line;

selecting one or more fertile progeny rice plants produced from the backcross of step b) having all of the physiological and morphological characteristics of the cytoplasmic male sterile line, except for increased stigma length;

backcrossing the one or more progeny rice plants selected in step c) with a rice plant from the stable cytoplasmic male sterile line as described herein; and selecting one or more progeny rice plants produced by the backcross of step d) having complete male sterility and all of the physiological and morphological characteristics of the cytoplasmic male sterile line, except for increased stigma length.

According to some embodiments of the invention, increased stigma length is selected when stigma length is at least 30% greater, at least 40% greater, at least 50% greater, or at least 60% greater than stigma length of rice plants of the maintainer line not introgressed with the long stigma trait of *Oryza longistaminata*.

According to some embodiments of the invention, the method further comprises detecting in progeny rice plants at least one marker for at least one *Oryza longistaminata* quantitative trait locus associated with stigma length and/or associated with total stigma and style length.

According to some embodiments of the invention, the at least one *Oryza longistaminata* quantitative trait locus associated with stigma length is selected from the group consisting of: qSTGL8-1 and qSTGL8-2.

According to some embodiments of the invention, the at least one marker for the QTL associated with stigma length is selected from the group consisting of PA08-03, RM7356, PX08-17 and PA08-18.

According to some embodiments of the invention, at least one *Oryza longistaminata* quantitative trait locus associated with total stigma and style length is selected from the group consisting of: qPSTL1-1; qPSTL1-3; and qPSTL11-1.

According to some embodiments of the invention, the at least one marker for the at least one *Oryza longistaminata* quantitative trait locus associated with total stigma and style length is selected from the group consisting of: RM3604 (qPSTL1-1); RM3746 (qPSTL1-1); RM3640 (qPSTL1-3); RM8134 (qPSTL1-3); and RM5997 (qPSTL11-1); RM254 (qPSTL11-1).

According to some embodiments of the invention, the stable cytoplasmic male sterile line is line IR58025A and the suitable maintainer line is IR58025B.

According to some embodiments of the invention, the stable cytoplasmic male sterile line is line IR68897A and the suitable maintainer line is IR68897B.

According to some embodiments of the invention, the stable cytoplasmic male sterile line is line IR127841A and the suitable maintainer line is IR127841B.

According to some embodiments of the invention, the stable cytoplasmic male sterile line is line IR127842A and the suitable maintainer line is IR127842B.

According to an aspect of some embodiments of the present invention there is provided a plant or plant part produced as described herein.

According to some embodiments of the invention, the plant part is a seed.

According to some embodiments of the invention, the cytoplasmic male sterile rice plant comprising a long stigma trait of *Oryza longistaminata* has an enhanced outcrossing rate relative to a cytoplasmic male sterile rice plant that does not comprise a long stigma trait of *Oryza longistaminata*.

According to some embodiments of the invention, the enhanced outcrossing rate presents as an increase in maximum percent of seed set.

According to some embodiments of the invention, the increase in maximum percent of seed set is selected from the group consisting of: a 2.5-fold increase; a 5-fold increase; a 10-fold increase; a 15-fold increase; a 20-fold increase; a 25-fold increase; a 30-fold increase; a 35-fold increase; a 40-fold increase; a 45-fold increase; a 50-fold increase; a 55-fold increase; a 60-fold increase; a 65-fold increase; a 70-fold increase; a 75-fold increase; an 80-fold increase; and an 85-fold increase.

According to an aspect of some embodiments of the present invention there is provided a method for increasing hybrid seed set in a rice plant comprising:

providing a cytoplasmic male sterile rice plant comprising a long stigma trait of *Oryza longistaminata*;

pollinating the cytoplasmic male sterile rice plant comprising a long stigma trait of *Oryza longistaminata* with pollen of a suitable restorer rice line; and enhancing hybrid rice seed set on the cytoplasmic male sterile rice plant comprising a long stigma trait of *Oryza longistaminata* relative to a cytoplasmic male sterile rice plant not having the long stigma trait of *Oryza longistaminata*.

According to some embodiments of the invention, the suitable restorer rice line is any rice line capable of pollinating the cytoplasmic male sterile rice plant comprising a long stigma trait of *Oryza longistaminata* to produce fertile hybrid seeds.

According to an aspect of some embodiments of the present invention there is provided a method for producing hybrid rice seed comprising:

carrying out the method as described herein; and collecting hybrid rice seed set on the cytoplasmic male sterile rice plant comprising the long stigma trait of *Oryza longistaminata*.

According to an aspect of some embodiments of the present invention there is provided a hybrid rice plant gown from the seed collected as described herein.

According to some embodiments of the invention, the hybrid rice plant outperforms its parents in at least one economically valuable agronomic trait relative to its parent plants.

According to some embodiments of the invention, outperformance in the at least one economically valuable agronomic trait is selected from the group consisting of: higher yield; higher uniformity; higher levels of disease resistance; higher levels of pest resistance; and increased drought tolerance.

According to an aspect of some embodiments of the present invention there is provided a method of producing rice meal, the method comprising:

(a) growing and collecting seeds of the hybrid rice plant; and (b) processing the seeds to meal.

In other embodiments described herein, increased stigma length is selected when stigma length is at least 30% greater, at least 40% greater, at least 50% greater, or at least 60% greater than stigma length of rice plants of the maintainer line not introgressed with the long stigma trait of *Oryza longistaminata*.

In another embodiment described herein, the stable cytoplasmic male sterile line is line IR58025A and the suitable maintainer line is IR58025B. In yet another embodiment, the stable cytoplasmic male sterile line is line IR68897A and the suitable maintainer line is IR68897B.

In another particular embodiment described herein is a plant or plant part produced by any one of methods described herein. In one embodiment, the plant part is a seed.

In another embodiment, the cytoplasmic male sterile rice plant comprising a long stigma trait of *Oryza longistaminata* has an enhanced outcrossing rate relative to a cytoplasmic male sterile rice plant that does not comprise a long stigma trait of *Oryza longistaminata*. The enhanced outcrossing rate can present as an increase in maximum percent of seed set. In certain embodiments, the increase in maximum percent of seed set is selected from the group consisting of: a 2.5-fold increase; a 5-fold increase; a 10-fold increase; a 15-fold increase; a 20-fold increase; a 25-fold increase; a 30-fold increase; a 35-fold increase; a 40-fold increase; a 45-fold increase; a 50-fold increase; a 55-fold increase; a 60-fold increase; a 65-fold increase; a 70-fold increase; a 75-fold increase; an 80-fold increase; and an 85-fold increase.

In a particular embodiment described herein is a method for increasing hybrid seed set in a rice plant comprising: a) providing a cytoplasmic male sterile rice plant comprising a long stigma trait of *Oryza longistaminata*; b) pollinating the cytoplasmic male sterile rice plant comprising a long stigma trait of *Oryza longistaminata* with pollen of a suitable restorer rice line; and c) enhancing hybrid rice seed set on the cytoplasmic male sterile rice plant comprising a long stigma trait of *Oryza longistaminata* relative to a cytoplasmic male sterile rice plant not having the long stigma trait of *Oryza longistaminata*. In certain embodiments, the suitable restorer rice line is any rice line capable of pollinating the cytoplasmic male sterile rice plant comprising a long stigma trait of *Oryza longistaminata* to produce fertile hybrid seeds.

In yet another particular embodiment described herein is a method for producing hybrid rice seed comprising: a) carrying out the method for increasing hybrid seed set in a rice plant; and b) collecting hybrid rice seed set on the cytoplasmic male sterile rice plant comprising the long stigma trait of *Oryza longistaminata*. In another particular embodiment is a hybrid rice plant grown from the collected seed.

In certain embodiments, the hybrid rice plant outperforms its parents in at least one economically valuable agronomic trait relative to its parent plants. The at least one economically valuable agronomic trait can be selected from the group consisting of: higher yield; higher uniformity; higher levels of disease resistance; higher levels of pest resistance; and increased drought tolerance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1: Schematic diagram showing breeding strategy for the development of cytoplasmic male sterile (CMS) rice lines introgressed with the long stigma trait of *Oryza longistaminata*. Top panel A) Development of maintainer lines with long stigma. Bottom panel B) Development of cMS lines with long stigma. *: Embryo rescue was carried out.

FIG. 2: Experimental design for hybrid seed production from control CMS lines IR68897A and IR58025A (not introgressed with the long stigma trait) and test CMS lines introgressed with the long stigma trait. The restorer (pollinator) line for all CMS lines tested was IR71604-4-1-4-4-4-2-2-2R.

Figure 3:
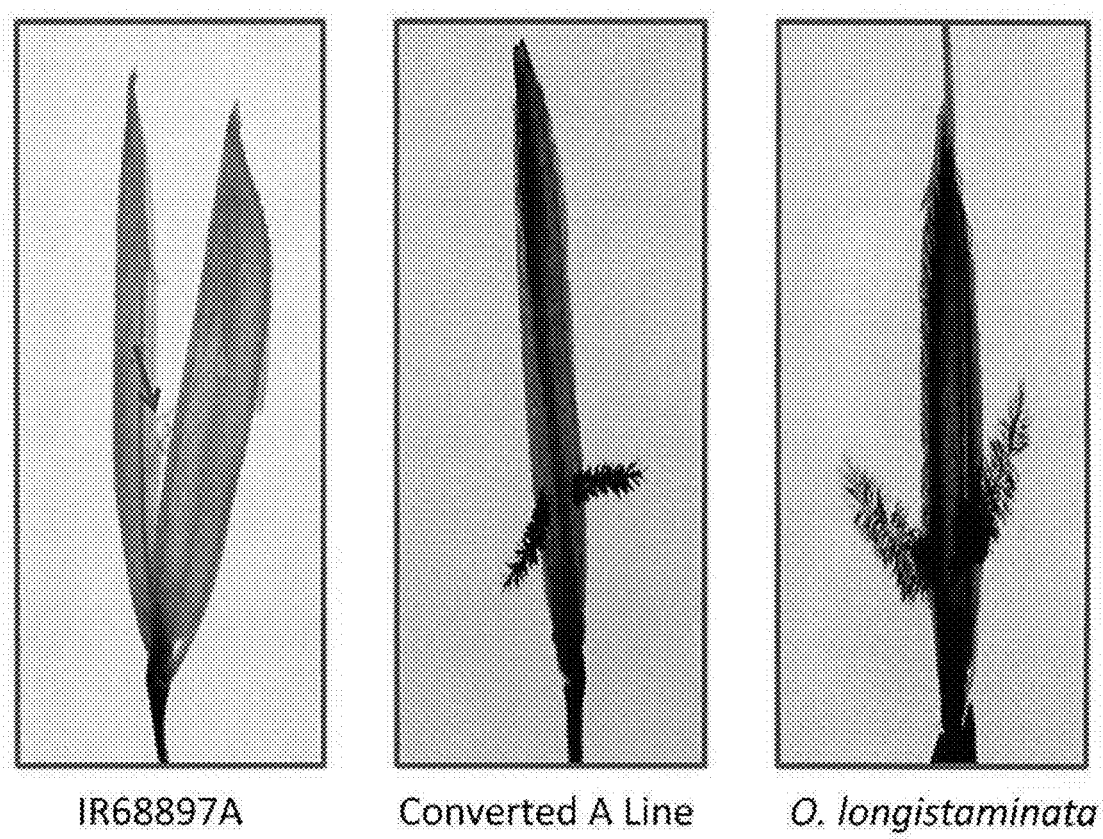

FIG. 3: Photographs showing variability in stigma length and exsertion in IR68897A, converted A line (introgressed with long stigma trait from *O. longistaminata*), and *O. longistaminata*.

Figure 4:
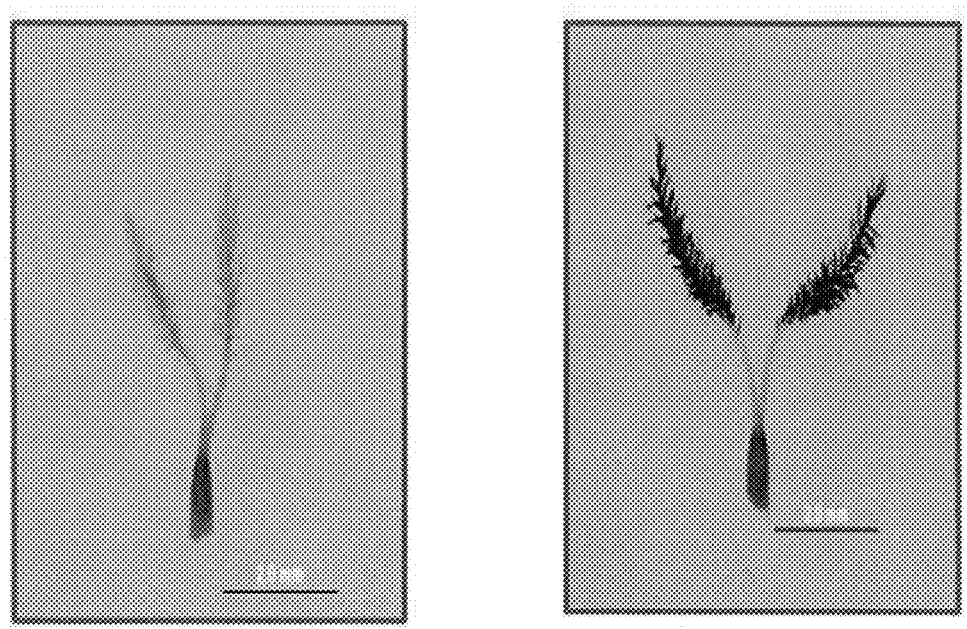

FIG. 4: Photographs showing increased stigma length in control CMS line IR68897 and an A line (OCF15-107-9) introgressed (converted) with the long stigma trait from *O. longistaminata*. IR68897A: stigma length=2.43±0.14 mm; stigma brush=1.58±0.12 mm. OCF15-107-9: stigma length=3.33±0.14*; stigma brush=2.54±0.12*. *: mean value significantly higher than IR68897A at $P<0.05$. Scale bar=2.0 mm FIG. 5: Table showing stigma length and width in converted A lines derived from *O. longistaminata* and control CMS line (IR68897A). *: mean values (mm) significantly higher than IR68897A at $P<0.05$.

Figures 6A, 6B:
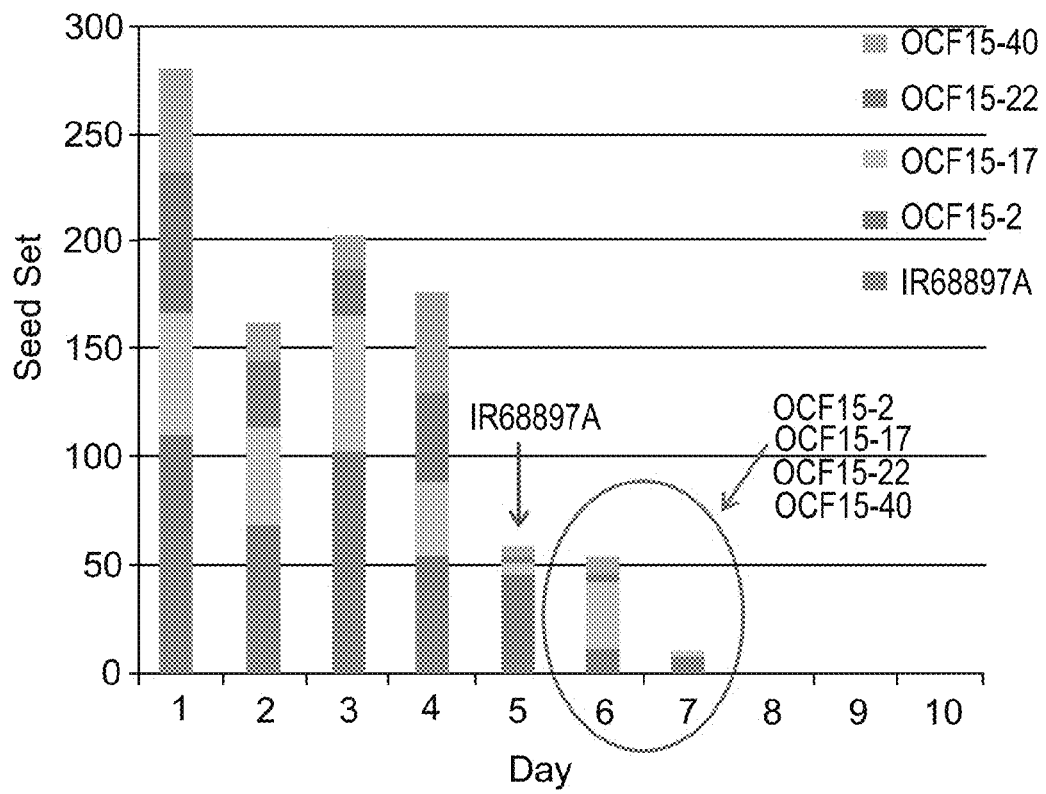

FIG. 6A: Table showing viability of converted A lines derived from *O. longistaminata* and control CMS line (IR68897A).

FIG. 6B: Bar graph showing viability of converted A lines derived from *O. longistaminata* and control CMS line (IR68897A).

Figure 7:
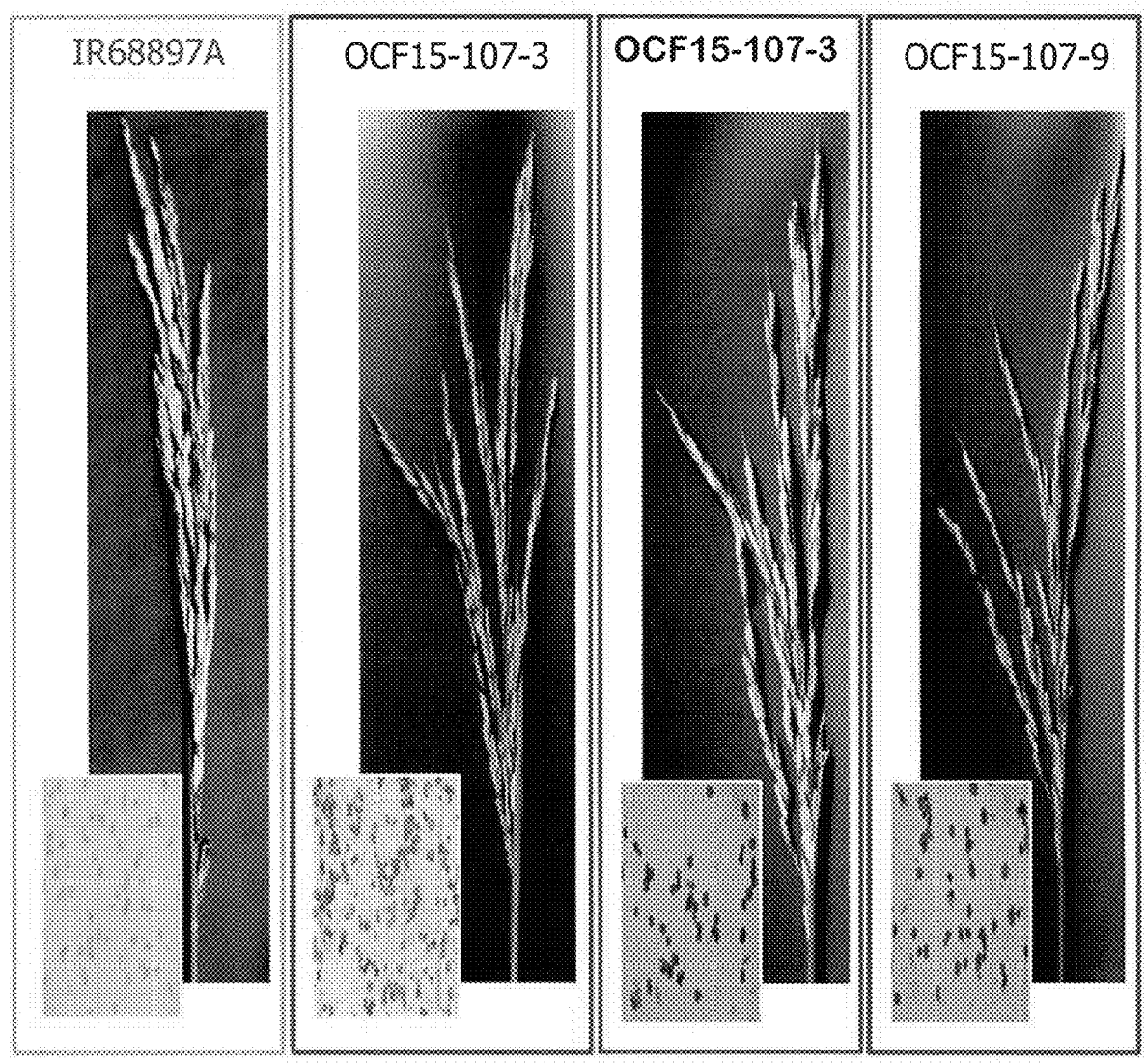

FIG. 7: Photographs and table showing sterility in control CMS line IR68897A, and seed set in two plants of converted line OCF15-107-3 and one plant of converted line OCF15-107-9.

FIG. 8: Table showing stigma brush length (mm), stigma non-brush length (mm), stigma total brush length (mm), stigma breadth (mm), and maximum seed set (%) in various converted A lines derived from *O. longistaminata* and control CMS line (IR68897A). Highlighted maximum seed set values indicate lowest (63.5%) and highest (80.5%) seed set values observed in the converted A lines.

FIG. 9A: Diagram showing linkage map of major QTLs identified for stigma length (qSTGL2-1, qSTGL5-1, qSTGL8-1, qSTGL8-2, qSTGL11-1 and qSTGL11-2) by composite interval mapping.

Figure 9B:
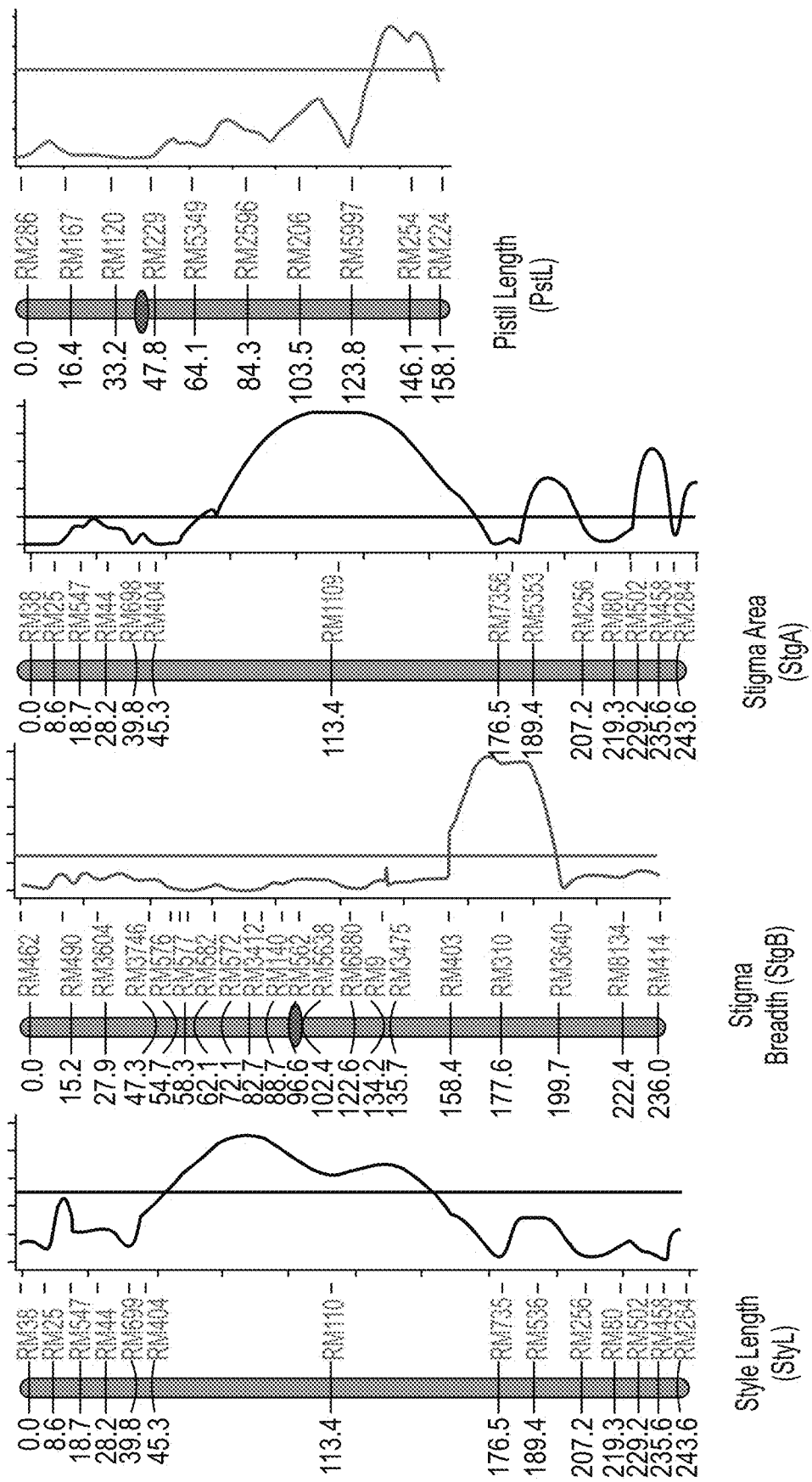

FIG. 9B: Diagram showing the linkage map of major QTLs identified for other floral traits except stigma length to improve out-crossing.

Figure 9C:
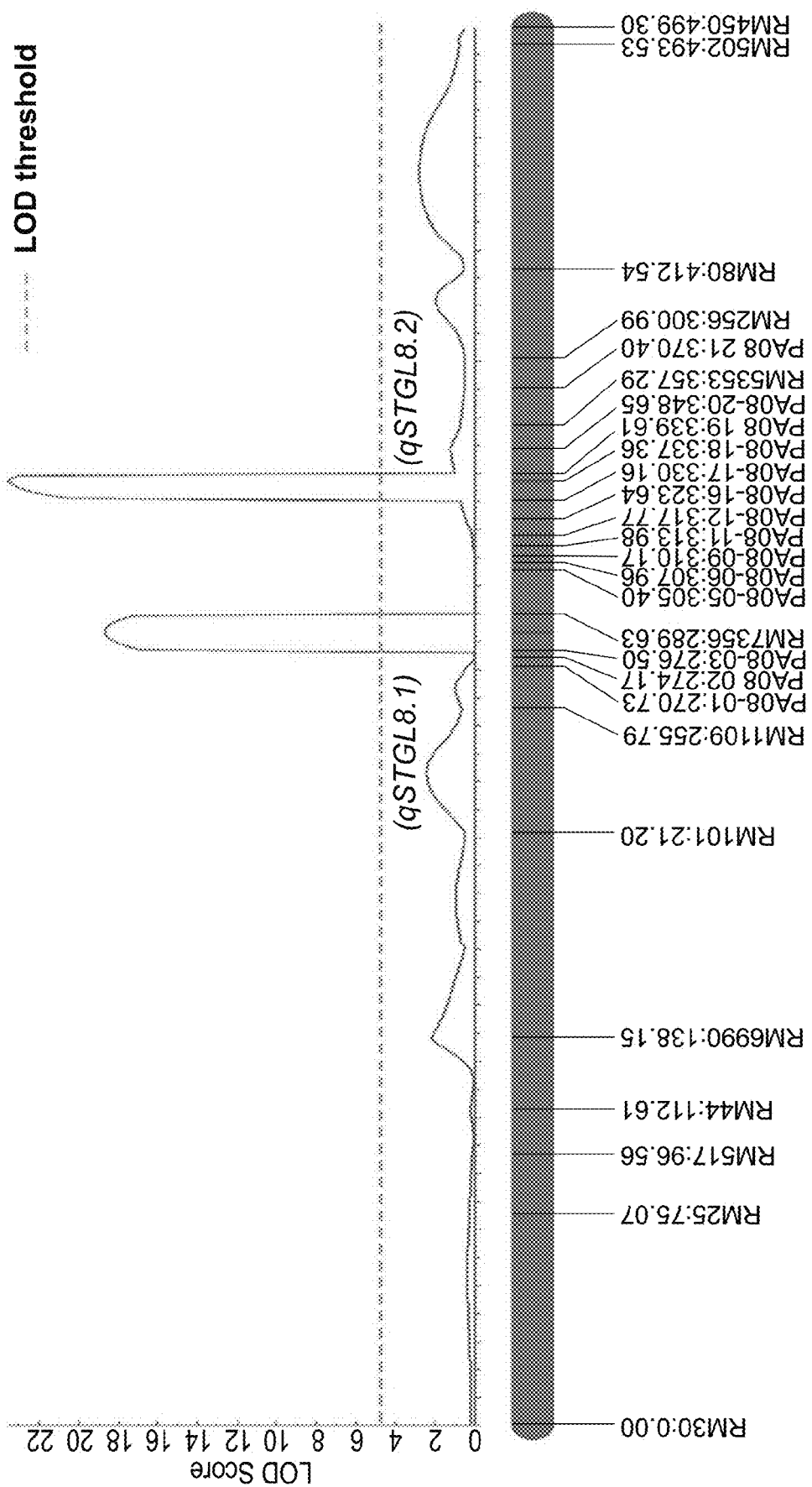

FIG. 9C Fine mapping of qSTGL8.0. The fine mapped putative qSTGL8.0 showed two sub-QTLs, the first is in between the *O. longistaminata* derived marker PA08-03 and RM 7356 (qSTGL8.1) and the other locus is between PA08-17 and PA08-18 markers (qSTGL8.2).

FIG. 9D Physical Mapping of qSTGL8.0. The qSTGL8.0 observed between SSR markers RM1109 and RM256 based on 357 $BC_2F_2$ segregants from IR-64×*O. longistaminata* dissected out by using newly designed InDel Markers. Numbers inside the parenthesis indicates number of recombinants of the respective marker.

FIG. 9E Region of the two putative loci positioned in between PA08-03 and RM356 and PA08-18 and PA08-19 markers.

Figure 9F:
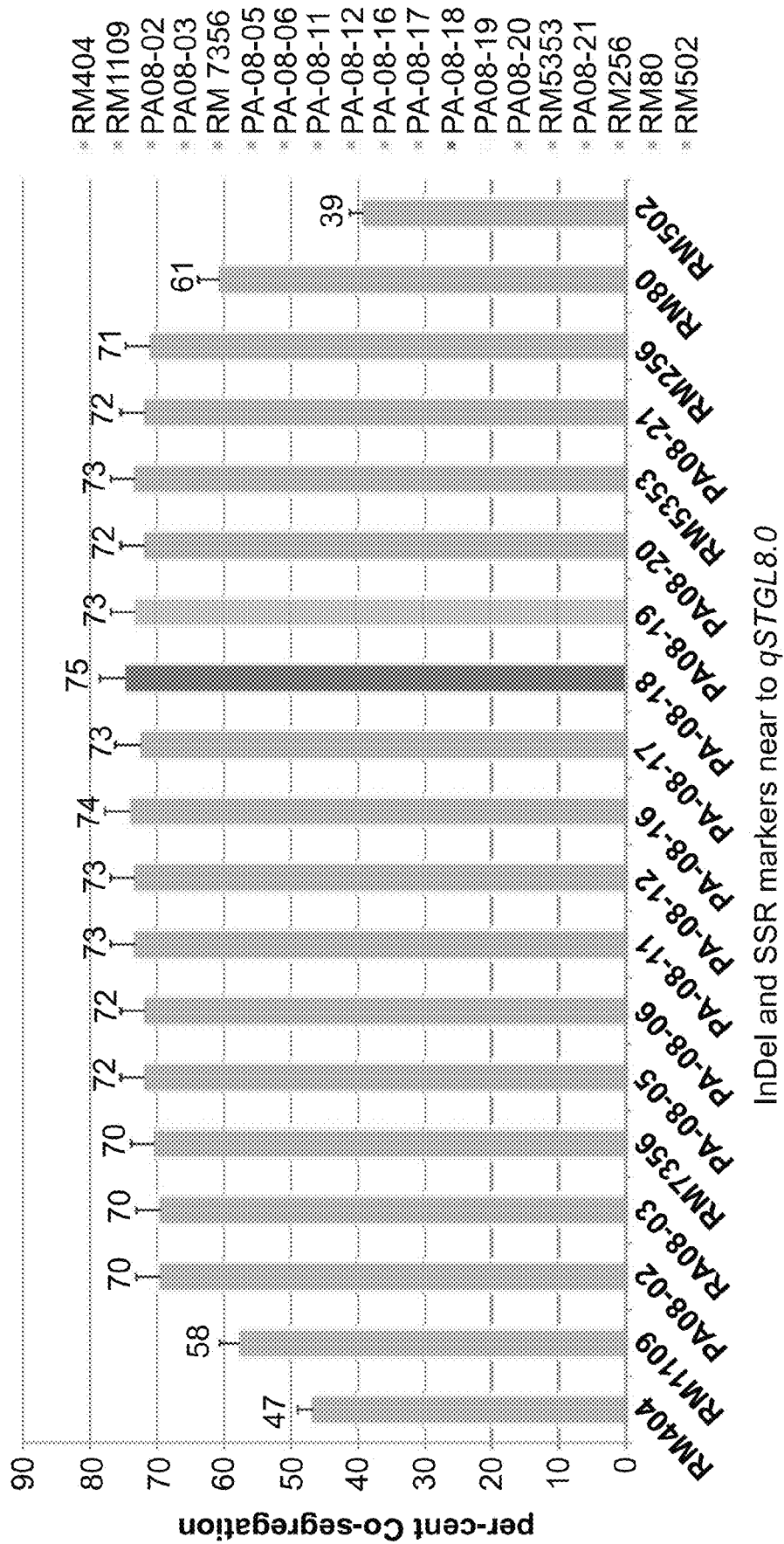

FIG. 9F Histogram showing percent co-segregation pattern of SSR and newly designed InDel markers near to qSTGL8.0. X-axis indicated InDel and SSR markers near to qSTGL8.0 and Y-axis indicated percent co-segregation. Values at each data point indicates percent co segregation of the respective marker. Histogram with dark green color bar indicated highest co-segregating marker PA08-18 with 75%.

FIG. 9G Agarose (3%) gel image showing the $BC_2F_3$ co-segregation pattern of PA08-18 new InDel *O. longistaminata* derived marker predicted to link to qSTGL8.2. Marker alleles were scored as 'A' for IR-64 alleles; 'B' for *O. longistaminata*(O.L) alleles and 'H' for heterozygous alleles of IR-64 and *O. longistaminata* for genotype score assessment. Phenotype below the genotype scores indicate stigma length phenotype of the respective $BC_2F_3$ individuals.

Figure 9H:
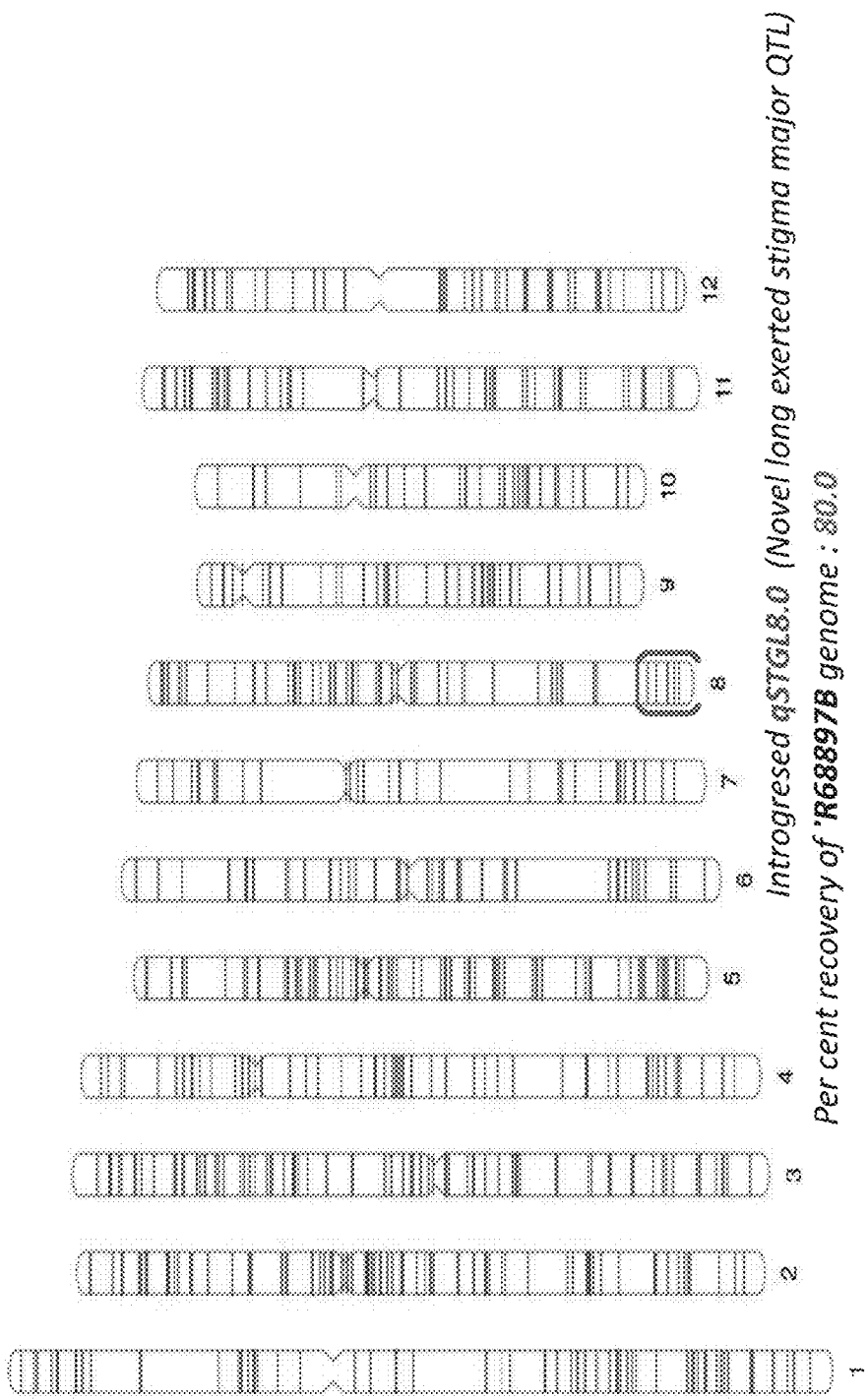

FIG. 9H Phenogram showing graphical genotypes of IR68897B derived improved CMS lines, IR127841A (OCF15-107-1-9). Numbers below each of the chromosomes indicate respective chromosome number, blue color lines indicate alleles of recurrent parent and red indicates alleles of donor parent and empty spaces indicate absence of SNPs at the respective positions.

FIG. 10: Photographs of pistils of *Oryza* species and related grass species. A) *O. sativa*, B) *O. nivara*, C) *O. rufipogon*, D) *O. glaberrima*, E) *O. barthii*, F) *O. longistaminata*, G) *O. meridionalis*, H) *O. glumaepatula*, I) *O. punctata*, J) *O. minuta*, K) *O. officinalis*, L) *O. rhizomatis*, M) *O. eichingeri*, N) *O. latifolia*, O) *O. alta*, P) *O. grandiglumis*, Q) *O. australiensis*, R) *O. brachyantha*, S) *O. granulata*, T) *O. meyeriana*, U) *O. ridleyi*, V) *O. longiglumis*, W) *O. coarctata*, X) *Rhychoryza subulata*, Y) *Leersia perrieri*.

FIG. 11: Photographs showing stigma exertion in IR68897B, IR68897B_Improved (converted), and IR68897A testcross progeny.

Figure 12:
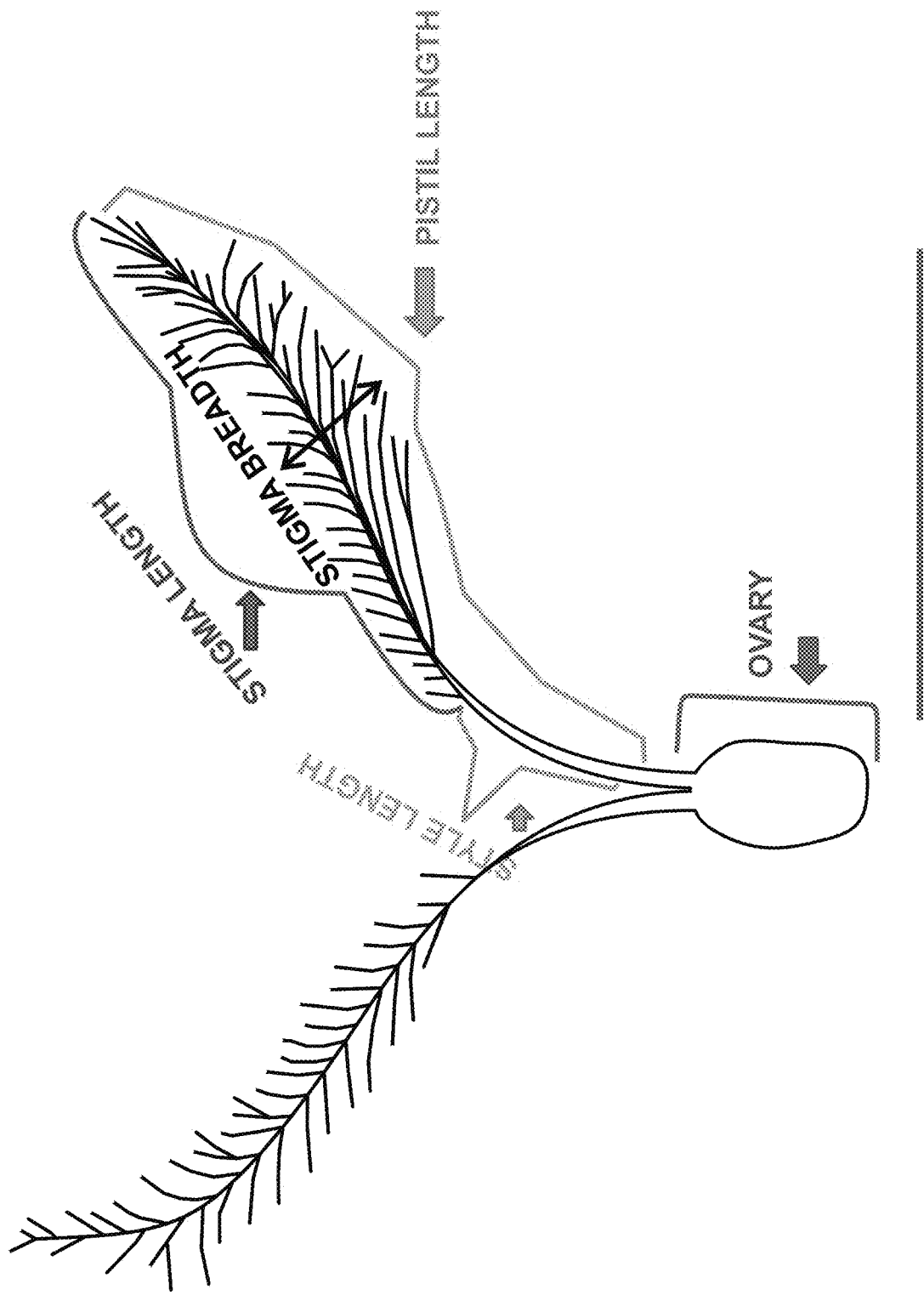

FIG. 12: Schematic diagram showing the different parts of the typical *Oryza longistaminata* female reproductive organ, Pistil.

DESCRIPTION OF SPECIFIC EMBODIMENTS OF THE INVENTION

The present invention, in some embodiments thereof, relates to rice plants with improved out-crossing rate, in particular embodiments of the invention relate to cytoplasmic male sterile rice plants with improved out-crossing rate and use thereof in the production of hybrid rice.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Definitions

So that the invention may be more readily understood, certain terms are first defined.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. According to a specific embodiment, the plant is a plant line.

According to a specific embodiment the plant line is an elite line. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like. According to a specific embodiment, the plant part comprises the nucleic acid sequence conferring long stigma from *Oryza longistaminata*. According to a specific embodiment, the plant part is a seed. According to a specific embodiment, the plant part is a hybrid seed.

As used herein, the phrases "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfings as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof, e.g., in this case male sterile having long stigma as described herein and a restorer line), while an F2 can be (and in some embodiments is) a progeny resulting from self-pollination of the F1 hybrids.

As used herein the term "cultivated *Oryza* plant" refers to a cultivated grass species having a diploid genome, 2n=24 (AA genome). Examples of domesticated *Oryza* species include but are not limited to, *Oryza sativa* (Asian rice) or *Oryza glaberrima* (African rice). The term may be interchanged with the term rice.

Domesticated *Oryza* varieties contemplated herein according to exemplary embodiments refer to long grain, short grain, white, brown, red and black.

There are three main varieties of *Oryza sativa:*

Indica: The indica variety is long-grained, for example Basmati rice, grown notably on the Indian sub-continent.

Japonica: Japonica rice is short-grained and high in amylopectin (thus becoming "sticky" when cooked), and is grown mainly in more temperate or colder regions such as Japan.

Javanica: Javanica rice is broad-grained and grown in tropical climates.

Other major varieties include Aromatic and Glutinos.

According to a specific embodiment, the rice variety contemplated herein is Indica.

According to a specific embodiment, the rice variety contemplated herein is *Japonica.*

According to a specific embodiment, the rice variety contemplated herein is Indica basmatic.

Within each variety, there are many cultivars, each favored for particular purposes or regions. Any genetic background of domesticated *Oryza* e.g., *Oryza sativa*, can be used. Other varieties and germplasms which can be used according to the present teachings are selected from the group consisting of: IR64; Nipponbare; PM-36, PS 36, Lemont, γS 27, Arkansas Fortuna, Sri Kuning, IR36, IR72, Gaisen Ibaraki 2, Ashoka 228, 1R74, NERICA 4, PS 12, Bala, Moroberekan, IR42, Akihikari, Nipponbare, IR20, IR56, IR66, NSIC Rc158, NSIC Rc222, and NSIC Rc238.

The term "crossed" or "cross" in the context of this invention means the fusion of gametes via pollination to produce progeny (i.e., cells, seeds or plants). The term encompasses both sexual crosses (the pollination of one plant by another) and selfing (self-pollination, i.e., when the pollen and ovule are from the same plant or from genetically identical plants).

"Backcrossing" is a process in which a breeder repeatedly crosses hybrid progeny back to one of the parents, for example, crossing a first generation hybrid F1 with one of the parental genotypes of the F1 hybrid. The parent to which the hybrid is backcrossed is the "recurrent parent."

Marker assisted selection may be used to augment or replace the phenotypic selection (such as by the use of molecular markers of chromosome 8).

Regardless of the selection method, following trait selection and backcrossing the genome of the domesticated rice plant of the recurrent parent is recovered to at least 85%, at least 87%, at least 90%, at least 92%, at least 94%, at least 96%, or at least 98%. That is, the plant of the invention has a genome being at least 85%, e.g., 85-99.9% that of the recurrent parent e.g., *Oryza sativa*.

Also provided are such methods, wherein the recovery of the recurrent rice plant's genome (e.g., *Oryza sativa*) is between 92% and 97%.

As used herein, "outcross" and "outcrossing" refers to cross-pollinations with a plant of differing genetic constitution, as opposed to self-pollination i.e., selfing. Preferably, the two plants or of a same kind, e.g., rice, e.g., cultivated rice e.g., *O. sativa* of the same subspecies e.g., *Japonica*, Indica etc.

"Outcrossing rate" refers to the rate that a particular plant pollinates or is pollinated by another plant. This is in contrast to self pollination.

"Improved outcrossing rate" or "increased outcrossing rate" refers to at least 50%, 60%, 70%, 80%, 90%, 100% or even 120%, 130%, 150% 200%, 250%, 300% or even more increase in outcrossing rate as compared to that of a non-converted plant of the same genetic background. An exemplary embodiment is provided in Table 3 in which an increase of at least 2.3 fold is evident.

Thus, according to some embodiment of the invention, the rice plant of the invention is endowed with an out-crossing rate which is more than 100% compared non-converted plant.

As used herein the term "heterosis" refers to hybrid vigor, or outbreeding enhancement, that is the improved or increased function of any biological quality in a hybrid offspring. An offspring exhibits heterosis if its traits are enhanced as a result of mixing the genetic contributions of its parents.

According to a specific embodiment, the increased outcrossing rate is manifested by an increase in maximum percent of seed set that can be selected from the group consisting of: a 1.5-fold increase, 2-fold increase, 2.5-fold increase; a 5-fold increase; a 10-fold increase; a 15-fold increase; a 20-fold increase; a 25-fold increase; a 30-fold increase; a 35-fold increase; a 40-fold increase; a 45-fold increase; a 50-fold increase; a 55-fold increase; a 60-fold increase; a 65-fold increase; a 70-fold increase; a 75-fold increase; an 80-fold increase; and an 85-fold increase.

"Yield" describes the amount of grain produced by a plant or a group, or crop, of plants. Yield can be measured in several ways, e.g. t ha$^{-1}$, and average grain yield per plant in grams.

The term "quantitative trait locus" or "QTL" refers to a polymorphic genetic locus with at least two alleles that reflect differential expression of a continuously distributed phenotypic trait.

As used herein, "introgression" means the movement of one or more genes, or a group of genes, from one plant variety into the gene complex of another as a result of breeding methods (e.g. outcrossing). Introgression also refers to movement of a trait encoded by one or more genes, or a group of genes, from one plant variety into the another.

"Converted" refers to a plant that has been introgressed with a trait of another plant. According to some embodiments, the term refers to a plant introgressed with the long stigma trait of *Oryza longistaminata*. Introgression of the trait may result from introgression of one or more QTLs associated with the trait. For example a "converted maintainer line" is a maintainer line introgressed with the long stigma trait of *Oryza longistaminata*.

A plant having "essentially all the physiological and morphological characteristics" of a specified plant refers to a plant having the same general physiological and morphological characteristics, except for those characteristics derived from a particular converted gene or group of genes (e.g., long stigma). The following definitions are further explained in FIG. 12.

As used herein "stigma length" refers to 'the total length consisting of brushy and non-brushy parts of the female reproductive organ which is pistil' A QTL associated with stigma length is abbreviated as "qSTGL".

As used herein "stigma area" refers to 'the length and breadth of stigma'. A QTL associated with stigma area is abbreviated as "qSTGA".

As used herein "style length" refers to the length of the stalk (filament) of the bifid stigma. A QTL associated with style length is abbreviated as "qSTYL".

As used herein "stigma breadth" refers to the distance or measurement from side to side of stigma (brushy) part'. A QTL associated with stigma breadth is abbreviated as "qSTGB".

As used herein "pistil length" or "total pistil length" which are interchangeably used refers to the total stigma length and style length. Although the word pistil includes ovary, style and stigma, the ovary length is not significantly different between the normal lines and the converted lines, Hence, total stigma and style length as pistil length. A QTL associated with pistil length is abbreviated as "qPSTL".

The term "associated with" or "associated" in the context of this invention refers to, for example, a QTL and a phenotypic trait (e.g., long stigma), that are in linkage disequilibrium, i.e., the QTL and the trait are found together in progeny plants more often than if the nucleic acid and phenotype segregated independently. The term "marker" or "molecular marker" or "genetic marker" refers to a genetic locus (a "marker locus") used as a point of reference when identifying genetically linked loci such as a QTL.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA of the long stigma introgression from *Oryza longistaminata*, whether from a rice plant or from a sample that includes DNA from the rice plant (e.g., meal). Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. According to some embodiment, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, .COPYRGT. 1991, Whitehead Institute for Biomedical Research, Cambridge, Mass.).

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template.

General Description

Heterosis is the phenomenon in which $F_1$ hybrids derived from diverse parents show superiority over their parents by displaying higher yield, higher uniformity, higher levels of disease resistance, higher levels of pest resistance, increased vigor, higher number of spikelets per panicle, higher number of productive tillers, etc. Heterosis is expressed in the first generation only. And while farmers tend to use a lower seed rate for hybrids than for conventional varieties because of their better seed quality relative to non-hybrids, it is necessary to purchase fresh seeds every season. The added expense of hybrid seeds, especially the difficult to produce rice hybrid seed, often puts the seed out of reach of the farmer.

Hybrid rice is developed by exploiting the phenomenon of heterosis. Rice, being a strictly self-pollinated crop, requires the use of a male sterility system to develop commercial rice hybrids. Male sterility (genetic or nongenetic) makes the pollen of the plant unviable, so that rice spikelets are incapable of setting seeds through selfing. A male sterile line is used as a female parent, and grown next to a pollen parent in an isolated plot to produce a bulk quantity of hybrid seed resulting from cross pollination from the pollen parent. The seed set on the male sterile plants is the hybrid seed that is used to grow the commercial hybrid crop.

The three-line method of hybrid rice breeding is based on cytoplasmic male sterility (CMS) and the fertility restoration system, and involves three lines: the CMS line (A line); maintainer line (B line), and restorer (pollinator; R line).

Male sterility is controlled by the interaction of a genetic factor S present in the cytoplasm and nuclear gene(s). The male sterility factor S is located in the mitochondrial DNA. A line is male sterile when the male sterility-controlling factor S in the cytoplasm and recessive alleles (rf) of fertility-restoring genes are present in the nucleus. The maintainer line (B line) is iso-cytoplasmic to the CMS line since it is similar to it for nuclear genes but differs in cytoplasmic factor (N), which makes it self-fertile, but it has the capacity to maintain the sterility of the A line when crossed with it. A restorer or R line possesses dominant fertility-restoring genes (Rf) and it is dissimilar to or diverse from the A line. Crossing a restorer line as a pollen parent with a CMS (A) line as a female parent restores the fertility in the derived $F_1$ hybrid, allowing plants grown from the hybrid seed to self pollinate and set seed.

Hybrid seed production using the CMS-based three-line method involves two basic steps: multiplication of the CMS line and production of hybrid seeds. Multiplication of the CMS line with its maintainer line by outcrossing by hand for a small quantity of seed, or in the field under isolation by space or time to produce bulk quantity of seed. For production of the CMS line, it is grown, for example, in six or eight rows interspersed by two rows of maintainer line in an alternating manner.

Because there usually small differences between the growth duration of A and B lines, their sowing dates can be adjusted to achieve good synchronization of their flowering. Several other techniques (including but not limited to flag-leaf clipping, gibberellic acid application, and supplementary pollination by rope pulling or shaking) are used to improve the outcrossing rate and seed yield of the CMS line.

The production of hybrid seeds involves the use of CMS lines with a selected restorer line (pollinator; R line) by growing them in a specific female:male ratio in the field under isolation by space or time (FIG. 2). The sowing dates of A and R lines are preferably staggered to achieve synchronization of their flowering. As in the maintenance step, outcrossing rate and hybrid set may be increased by methods including but not limited to flag-leaf clipping, gibberellic acid application, and supplementary pollination by rope pulling or shaking.

The extent of outcrossing in the female seed parent (CMS line) is influenced by floral traits such as stigma size (length and breadth), length of style, stigma exsertion, and angle and duration of glume opening. The length of stigma and style, and total length (stigma+style), were characterized in 47 accessions of the 24 species of Oryza (Table XX of Example 1). Oryza longistaminata, a wild species of the AA genome, had significantly long and wider stigma, longer style, and greater total length than the other species. Oryza longistaminata was thus identified as a potential donor for the long stigma trait.

Oryza longistaminata (acc. no. 110404) is first crossed with a maintainer line, thereby introgres sing the long and wide stigma trait into one or more plants of the maintainer line. Any maintainer line can be crossed with Oryza longistaminata. In particular embodiments, the two popular indica maintainer lines IR58025B and IR68897B are crossed with Oryza longistaminata, thereby introgressing the long and wide stigma trait into at least one plant of the maintainer line. Progeny are selected for long and wide stigma in $F_1$, $BC_1F_1$, $BC_2F_1$, and their segregating generations. FIG. 1 (top panel) depicts the general strategy for introgressing the long and wide stigma trait of *Oryza longistaminata* into a maintainer line.

In one embodiment, $F_1$ progeny are backcrossed with a rice plant of the maintainer line to produce a $BC_1F_1$ generation. Fertile $BC_1F_1$ with increased stigma length relative to rice plants of the maintainer line are selected for backcrossing. Backcrossing with the recurrent parent can be done 1 to 5 times, producing $BC_2F_1$ to $BC_6F_1$ progeny rice plants. Fertile progeny are again selected, where selected plants have all the physiological and morphological characteristics of the maintainer line, except for the desired trait of increased stigma length. Selected plants are intercrossed or selfed to produce $F_2$ or later generations, which are stable for the long stigma trait. Those skilled in the art will recognize that modifications to this general strategy may be made, but still result in a converted maintainer line. Such modifications are to be recognized as being within the scope of the present invention.

In certain embodiments, progeny plants of a cross between *Oryza longistaminata* and the maintainer line, or later backcross progeny, are produced via embryo rescue.

The long and wide stigma trait is then introgressed into a cytoplasmic male sterile (CMS) line by crossing the CMS line with a corresponding maintainer line, wherein the corresponding maintainer line expresses the long and wide stigma trait derived from *Oryza longistaminata* (i.e., converted). For example, CMS line IR58025A is crossed with selected IR58025B progeny from the cross with *Oryza longistaminata*, where the selected progeny express the long and wide stigma trait. CMS line IR68897A is crossed with long and wide stigma-introgressed maintainer line IR68897A. Other CMS lines can be similarly crossed with selected plants of an appropriate maintainer line, where the selected plants express the long and wide stigma trait of *Oryza longistaminata*. Progeny of the CMS×converted maintainer line are selected for long and wide stigma. In certain embodiments, fertile $F_1$ progeny with long stigma are backcrossed with the CMS recurrent parent line, followed by backcrossing fertile $BC_1F_1$ progeny with long stigma with the CMS recurrent parent. Backcross progeny with complete male sterility and long stigma are selected. In some embodiments, backcross progeny with complete male sterility and long stigma are selected for generating a stable CMS line having long stigma. The stable CMS line is preferably generated by backcrossing. FIG. 1 (bottom panel) depicts the general strategy for introgressing the long and wide stigma trait of *Oryza longistaminata*, first introduce into the maintainer line, into a CMS line. Those skilled in the art will recognize that modifications to this general strategy may be made (e.g., additional backcrossing), but still result in a converted CMS line. Such modifications are to be recognized as being within the scope of the present invention.

In certain embodiments of the breeding methods described above, increased stigma length is selected when stigma length is at least 30% greater, at least 40% greater, at least 50% greater, or at least 60% greater than stigma length of rice plants of the maintainer line not introgressed with the long stigma trait of *Oryza longistaminata*. In a preferred embodiment, increased stigma length is selected when stigma length is at least 50% greater than stigma length of rice plants of the maintainer line not introgressed with the long stigma trait of *Oryza longistaminata*.

Converted CMS lines are then pollinated by a restorer line comprising a dominant fertility-restoring genes (Rf; FIG. 2). Any restorer line capable of restoring fertility in the converted CMS can be used. In one embodiment, the restorer line is IR71604-4-4-4-2-2-2R. Hybrid seed resulting from the converted CMS×restorer cross is set on plants of the converted CMS line. The hybrid seed is then collected for future planting. As shown in the Examples and figures, CMS lines introgressed with the long and wide stigma trait of *Oryza longistaminata* have significantly longer stigma brushes and greater total stigma length than their recurrent CMS parent (FIGS. 3-5, 11). This increased stigma length results in improved stigma viability (FIGS. 6A-B), and outcrossing rates, as observed by significant increases in seed set (FIGS. 7-8). For example, a maximum percentage of seed set of 5-20% was observed for CMS line IR68897A. Converted CMS lines having longer stigma's than the control had maximum percentage of seed set from 63.5% to 80.5%, or about a 3-fold to about a 16-fold increase in percent of seed set. In particular embodiments, the increase in maximum percent of seed set ranges from about 2.5-fold to about 85-fold.

In particular embodiments, the converted CMS line, restorer line, or both, comprise one or more desirable agronomic characteristics. Desirable agronomic characteristics include, but are not limited to semi-dwarf plant height, high yield, uniformity, bacterial leaf blight disease resistance, brown planthopper pest resistance, and/or drought tolerance. In a preferred embodiment, rice grown from hybrid seed set on converted CMS lines described herein outperforms its parents in at least one desirable agronomic characteristic. For example, hybrid seeds described herein can result in higher yield, higher uniformity, higher levels of disease resistance, higher levels of pest resistance, and/or improved drought tolerance.

Thus, in an aspect of the invention there is provided a cultivated rice plant comprising an introgression including at least one *Oryza longistaminata* quantitative trait locus (QTL) associated with stigma length, the cultivated rice plant having an out-crossing rate of at least 60%.

In an aspect of the invention there is provided a cultivated rice plant comprising an introgression including at least one *Oryza longistaminata* quantitative trait locus (QTL) associated with stigma length selected from the group consisting of: qSTGL8-1 and qSTGL8-2.

In one particular embodiment, the rice plant is a cytoplasmic male sterile line.

In one particular embodiment, the rice plant is a maintainer line.

In one particular embodiment, the rice plant has an out-crossing rate of at least 60% (or as described herein).

In one particular embodiment, the rice plant comprises at least an additional introgression including at least one *Oryza longistaminata* QTL associated with stigma length, stigma area, style length, stigma breadth or total pistil length.

In one particular embodiment, the at least one *Oryza longistaminata* QTL associated with stigma length, stigma area, style length, stigma breadth and pistil length is selected from the group consisting of qSTGL2-1, qSTGL5-1, qSTGL8-1, qSTGL8-2, qSTGL11-1, qSTGL11-2; qSTGA8-2; qSTYL1-1, qSTYL5-2, qSTYL8-1; qSTGB1-1, qSTGB3-1; qPSTL1-1, qPSTL1-3 and qPSTL11-1.

In one particular embodiment, a marker of the at least one additional QTL is selected from the group consisting of stigma length, RM110 (qSTGL2-1), RM421 (qSTGL5-1), RM7356 (qSTGL8-1), RM5353 (qSTGL8-1), RM256 (qSTGL8-2), RM80 (qSTGL8-2), RM590 (qSTGL11-1), RM286 (qSTGL11-1), RM 120 (qSTGL11-2); RM229 (qSTGL11-2); stigma area, RM80 (qSTGA8-2); style length, RM319 (qSTYL1-1), RM7653 (qSTYL5-2), RM404 (qSTYL8-1); stigma breadth, RM403 (qSTGB1-1), RM3525 (qSTGB3-1); and pistil length, RM3604 (qPSTL1-1); RM3640 (qPSTL1-3); and RM5997 (qPSTL11-1).

In one particular embodiment, at least one marker for the QTL associated with stigma length is selected from the group consisting of PA08-03, RM7356, PA08-17 and PA08-18.

In one particular embodiment, the introgression comprising QTL associated with stigma length is positioned between markers PA08-03 to RM7356 or PA08-17 to PA08-18.

In one particular embodiment, the rice plant is a line selected from the group consisting of IR68897A, IR58025A, IR127841A and IR127842A.

In an aspect of the invention there is provided a hybrid rice plant having the rice plant having the long stigma, as described herein, as a parent or an ancestor.

In an aspect of the invention there is provided a tissue culture produced from protoplasts or cells from the rice plant having the long stigma, as described herein, wherein the protoplasts or cells of the tissue culture are produced from a plant part selected from the group consisting of: leaves; pollen; embryos; cotyledon; hypocotyls; meristematic cells; roots; root tips; pistils; anthers; flowers; stems; glumes; and panicles.

In an aspect of the invention there is provided a rice plant regenerated from the tissue culture, wherein the rice plant is a cytoplasmic male sterile rice plant having all the morphological and physiological.

In one particular embodiment, a CMS plant of line IR58025A is bred by the methods described herein to comprise the long stigma trait of *Oryza longistaminata*. A suitable maintainer line for the converted CMS line IR58025A is line IR58025B. In another particular embodiment, a CMS plant of line IR68897A is bred by the methods described herein to comprise the long stigma trait of *Oryza longistaminata*. A suitable maintainer line for the converted CMS line IR68897A is line IR68897B.

In another aspect, the present invention provides regenerable cells for use in tissue culture of a CMS plant comprising the long stigma trait of *Oryza longistaminata*. The tissue culture will preferably be capable of regenerating plants having the physiological and morphological characteristics of the foregoing rice plant, and of regenerating plants having substantially the same genotype. Preferably, the regenerable cells in such tissue cultures will be produced from embryo, protoplast, meristematic cell, callus, pollen, leaf, stem, petiole, root, root tip, fruit, seed, flower, anther, pistil or the like. Still further, the present invention provides converted CMS rice plants regenerated from tissue cultures of the invention.

Marker Assisted Selection of Converted Maintainer Lines and CMS Lines

In another embodiment described herein, the development of converted maintenance and CMS lines is enhanced by marker assisted selection. Basic protocols for marker assisted selection are well known to one of ordinary skill in the art. Given the benefit of this disclosure, including the quantitative trait loci (QTLs) and markers described herein, one of skill in the art will be able to carry out the invention as described.

A genetic mapping population is generated by crossing *Oryza longistaminata* with a variety of cultivated rice (e.g., IR64). Markers associate with genomic regions controlling stigma length (e.g., QTLs) can then be identified via molecular mapping. These markers are then used to aid in selecting rice plants of maintainer or CMS lines successfully introgressed with the long stigma trait of *Oryza longistaminata*.

A single plant of *Oryza longistaminata* was crossed with the high yielding cultivar IR64, as described in Example 6. The linkage map of the detected QTLs are shown in FIGS. 9A and B. A total of 15 QTLs were identified by composite interval mapping for five floral traits, including stigma length (6 QTLs), style length (3 QTLs), stigma breadth (2 QTLs), stigma area (1 QTL), and total pistil length (3 QTLs) (TABLE 5 of Example 6).

Marker-assisted selection (MAS) involves the use of one or more of the molecular markers for the identification and selection of those progeny plants that contain one or more of the genes that encode for the desired trait. In the present instance, such identification and selection is based on the long and wide stigma trait of *Oryza longistaminata*, and QTLs of the present invention or markers associated therewith. MAS can be used to select progeny plants having the desired trait during the development of the converted maintainer and/or CMS lines by identifying plants harboring the QTL(s) of interest, allowing for timely and accurate selection. Rice plants developed according to this embodiment can advantageously derive a majority of their traits from the recipient plant (i.e., plant of maintainer or CMS line), and derive the long stigma trait from the donor plant (*Oryza longistaminata*).

In certain embodiments, one or more markers in progeny plants during the development of converted maintainer lines, converted CMS lines, or both. Detection of one or more markers in a converted line, wherein the marker is linked to a QTL of *Oryza longistaminata* associated with stigma length and/or total length of stigma and style, is indicative of introgression of the target trait. The QTL can be any one of those QTLs of Table 5 associated with stigma length and/or total length of stigma and style. A QTL of the present invention is detected using any marker associated with a given QTL, as provided in Table 5. In a particular embodiment, the QTL detected is at least one *Oryza longistaminata* quantitative trait locus associated with stigma length is selected from the group consisting of: qSTGL2-1; qSTGL5-1; qSTGL8-1; qSTGL8-2 and qSTGL11-1. At least one marker for at least one *Oryza longistaminata* quantitative trait locus associated with stigma length is selected from the group consisting of: RM110 (qSTGL2-1); RM421 (qSTGL5-1); RM7356 (qSTGL8-1); RM5353 (qSTGL8-1); RM256 (qSTGL8-2); RM80 (qSTGL8-2); RM590 (qSTGL11-1); RM286 (qSTGL11-1); RM120 (qSTGL11-2); and RM229 (qSTGL11-2). The QTLs detected for other floral traits are qPSTL1-1; qPSTL1-3; and qPSTL11-1. At least one marker for at least one *Oryza longistaminata* quantitative trait locus associated with total stigma and style length can be selected from the group consisting of: RM3604 (qPSTL1-1); RM3640 (qPSTL1-3); and RM5997 (qPSTL11-1).

According to an exemplary embodiment, the introgression of qSTGL8-1; qSTGL8-2 can be detected using SEQ ID NOs: 13, 14 and 9, 10 (The InDel marker, PA08-18 or PA08-03).

Primers which can be used to detect the introgressions described according to some embodiments of the invention are listed in Table 8, which is considered as part of the general specification.

Also contemplated are primers, probes, amplicons and/or kits comprising same which can be diagnostic of the introgression of the invention (long stigma from *Oryza logistaminata*).

The nucleic acid probes and primers of the present invention hybridize under stringent conditions to a target DNA sequence. Any conventional nucleic acid hybridization or amplification method can be used to identify the presence the long stigma introgression from *Oryza longistaminata* in a sample. Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: Nucleic Acid Hybridization, A Practical Approach, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

For example, to determine whether the rice plant resulting from a sexual cross contains the long stigma introgression from *Oryza longistaminata* from the rice plant of the present invention, DNA extracted from a rice plant tissue sample (e.g., endosperm of a seed/meal/grain of a rice plant having long stigma as described herein e.g., of a hybrid plant) may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the long stigma introgression from *Oryza longistaminata*. The amplicon is of a length and has a sequence that is also diagnostic for the long stigma introgression from *Oryza longistaminata*. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the introgression or flanking sequence can be verified (and corrected if necessary) by amplifying such sequences from the long stigma introgression from *Oryza longistaminata* using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTP's are added individually and the incorporation results in a light signal which is measured. A light signal indicates the presence of the long stigma introgression from *Oryza longistaminata* due to successful amplification, hybridization, and single or multi-base extension.

Fluorescence polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorimeter. A change in polarization indicates the presence of the long stigma introgression from *Oryza longistaminata* due to successful amplification, hybridization, and single base extension.

Taqman®. (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the long stigma introgression from *Oryza longistaminata* due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the long stigma introgression from *Oryza longistaminata* due to successful amplification and hybridization.

Other described methods, such as, microfluidics (US Patent pub. 2006068398, U.S. Pat. No. 6,544,734) provide methods and devices to separate and amplify DNA samples. Optical dyes used to detect and quantitate specific DNA molecules (WO/05017181). Nanotube devices (WO/06024023) that comprise an electronic sensor for the detection of DNA molecules or nanobeads that bind specific DNA molecules and can then be detected.

DNA detection kits are provided using the compositions disclosed herein. The kits are useful for the identification of the long stigma introgression from *Oryza longistaminata* in a sample and can be applied at least to methods for breeding rice plants containing the appropriate introgressed DNA. The kits contain DNA primers and/or probes that are homologous or complementary to segments selected from the sequences as set forth at SEQ ID NO: 1-56, as set forth in the Sequence Listing. These DNA sequences can be used in DNA amplification reactions or as probes in a DNA hybridization method for detecting the presence of polynucleotides diagnostic for the presence of the target DNA in a sample. The production of a predefined amplicon in a thermal amplification reaction is diagnostic for the presence of DNA corresponding to the long stigma introgression from *Oryza longistaminata* in the sample. If hybridization is selected, detecting hybridization of the probe to the biological sample is diagnostic for the presence of the long stigma introgression from *Oryza longistaminata* in the sample. Typically, the sample is rice, or rice products or by-products of the use of rice. Also provided are processed rice products which are produced from the plants described herein and preferably contain the nucleic acid sequence conferring the improved out-crossing rate described herein. Also provided are methods of processing the rice (e.g., to produce meal) or other processed products.

Food Characteristics:

Rice starch is a major source of carbohydrate in the human diet, particularly in Asia, and the grain of the invention and products derived from it can be used to prepare food. The food may be consumed by man or animals, for example in livestock production or in pet-food. The grain derived from the rice plant can readily be used in food processing procedures, and therefore the invention includes milled, ground, kibbled, cracked, rolled, boiled or parboiled grain, or products obtained from the processed or whole grain of the rice plant, including flour, brokers, rice bran and oil. The products may be precooked or quick-cooking rice, instant rice, granulated rice, gelatinized rice, canned rice or rice pudding. The grain or starch may be used in the production of processed rice products including noodles, rice cakes, rice paper or egg roll wrapper, or in fermented products such as fermented noodle or beverages such as sake. The grain or starch derived therefrom may also be used in, for example, breads, cakes, crackers, biscuits and the like, including where the rice flour is mixed with wheat or other flours, or food additives such as thickeners or binding agents, or to make drinks, noodles, pasta or quick soups. The rice products may be suitable for use in wheatfree diets. The grain or products derived from the grain of the invention may be used in breakfast cereals such as puffed rice, rice flakes or as extruded products.

Dietary Fiber:

Dietary fiber, in this specification, is the carbohydrate and carbohydrate digestion products that are not absorbed in the small intestine of healthy humans but enter the large bowel. This includes resistant starch and other soluble and insoluble carbohydrate polymers. It is intended to comprise that portion of carbohydrates that are fermentable, at least partially, in the large bowel by the resident microflora.

Non-Food Applications:

Rice is widely used in non-food industries, including the film, paper, textile, corrugating and adhesive industries, for example as a sizing agent. Rice starch may be used as a substrate for the production of glucose syrups or for ethanol production.

DNA detection in the processed products can be performed using methods which are well known in the art and are described in some detail hereinabove.

Thus, the markers can be to any of the loci (e.g., Table 5) described herein which are associated with high out-cross rate.

According to some exemplary embodiments, the DNA locus is a quantitative trait locus associated with stigma length which can be selected from the group consisting of: qSTGL2-1; qSTGL5-1; qSTGL8-1; qSTGL8-2 and qSTGL11-1. At least one marker for at least one *Oryza longistaminata* quantitative trait locus associated with stigma length is selected from the group consisting of: RM110 (qSTGL2-1); RM421 (qSTGL5-1); RM7356 (qSTGL8-1); RM5353 (qSTGL8-1); RM256 (qSTGL8-2); RM80 (qSTGL8-2); RM590 (qSTGL11-1); RM286 (qSTGL11-1); RM120 (qSTGL11-2); and RM229 (qSTGL11-2).

In another embodiment described herein, at least one *Oryza longistaminata* quantitative trait locus associated with total stigma and style length can be selected from the group consisting of: qPSTL1-1; qPSTL1-3; and qPSTL11-1. At least one marker for at least one *Oryza longistaminata* quantitative trait locus associated with total stigma and style length can be selected from the group consisting of: RM3604 (qPSTL1-1); RM3640 (qPSTL1-3); and RM5997 (qPSTL11-1).

Exemplary markers for validation of the long stigma trait are provided as follows: PA08-03 (GCTCTCTA-CATGCCCTCGT; CCGTGTGTTGGTAGGTCAGA) and PA08-18 (GATCAATGTTTGGTCACCATCC; GTAGTCTCCTGCAATATCCC, SEQ ID NOs: 9, 10, 13 and 14). These are Indel markers we designed by genome sequence comparison between *O. longistaminata* and Nipponbare (*O. sativa*).

It is expected that during the life of a patent maturing from this application many relevant markers will be developed and the scope of the term marker is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

The materials, methods, and embodiments described herein are further defined in the following Examples. Certain embodiments of the present invention are defined in the Examples herein. It should be understood that these Examples, while indicating certain embodiments of the invention, are given by way of illustration only. From the discussion herein and these Examples, one skilled in the art can ascertain the essential characteristics of this invention and without departing from the spirit and scope thereof, can make various changes and modifications of the invention to adapt it to various usages and conditions.

Example 1. Characterization of Pistil Traits of *Oryza* Species to Identify Wild Species as Donors for Transferring Floral Traits Influencing Outcrossing To understand the variability of pistil traits, stigma length, stigma width, style length, and to stigma and style length were characterized in 47 accessions of the 24 species of genus *Oryza* covering eleven genomes, including cultivated rice and two unrelated plant species (Table 1; FIG. 10). The data from *O. schelcteri* were not collected as it never flowers under tropical conditions. The cultivars of *O. sativa* subspecies *japonica* have significantly shorter stigma, style, and total length than indica cultivars. Among the wild species of the AA genome, *O. longistaminata* has significantly longer and wider stigma, style, and total length than the remaining species. At the genome complex level, the *O. ridleyi* complex has a significantly longer stigma than the *O. sativa* complex and *O. officinalis* complex. The total length of the stigma and style of the *O. meyeriana* complex and *O. ridleyi* complex was significantly longer than that of the *O. sativa* and *O. officinalis* complexes. Total length showed a high positive association with stigma length.

Size variation was not observed for style length in cultivated and wild species. In our study, we observed that cultivated rice tends to have a shorter stigma than the annual wild species (*O. nivara* and *O. barthii*) which are shorter than the perennial progenitors. Among the AA genome wild species, *O. longistaminata*, which has longer stigma and style lengths than the remaining species, can be utilized for transfer of longer and wider stigma into maintainer and CMS lines to increase hybrid rice seed production.

TABLE 1

Length characteristics of stigma, style, and their total length in *Oryza* spp.

| | Stigma length | | | | Style length | | | | Total length | | | |
|---|---|---|---|---|---|---|---|---|---|---|---|---|
| Species | Min | Max | Mean | SD | Min | Max | Mean | SD | Min | Max | Mean | SD |
| Intraspecific | | | | | | | | | | | | |
| *Indica* | 0.98 | 1.40 | 1.22 | 0.12 | 1.02 | 1.42 | 1.21 | 0.13 | 2.18 | 2.74 | 2.43 | 0.18 |
| *Japonica* | 0.67 | 1.06 | 0.88 | 0.11 | 0.64 | 1.09 | 0.86 | 0.14 | 1.32 | 2.15 | 1.74 | 0.24 |
| F value | | | 48.76** | | | | 60.46** | | | | 71.85** | |
| LSD 1% | | | 0.14 | | | | 0.13 | | | | 0.23 | |
| AA genome level | | | | | | | | | | | | |
| *O. sativa* | 0.67 | 1.40 | 1.10 | 0.20 | 0.64 | 1.42 | 1.09 | 0.21 | 1.32 | 2.74 | 2.20 | 0.39 |
| *O. nivara* | 0.80 | 1.86 | 1.29 | 0.46 | 0.50 | 1.20 | 0.92 | 0.21 | 1.30 | 3.06 | 2.21 | 0.66 |
| *O. rufipogon* | 1.48 | 2.10 | 1.74 | 0.22 | 0.81 | 1.11 | 0.97 | 0.10 | 2.44 | 3.21 | 2.71 | 0.30 |
| *O. glaberrima* | 0.86 | 1.11 | 1.01 | 0.08 | 0.79 | 0.90 | 0.86 | 0.04 | 1.69 | 2.01 | 1.87 | 0.10 |
| *O. barthii* | 1.42 | 2.22 | 1.74 | 0.29 | 0.87 | 1.33 | 1.01 | 0.12 | 2.33 | 3.31 | 2.76 | 0.38 |
| *O. longistaminata* | 2.49 | 3.37 | 2.87** | 0.28 | 1.18 | 1.50 | 1.32** | 0.10 | 3.80 | 4.87 | 4.19** | 0.35 |
| *O. meridionalis* | 0.91 | 1.88 | 1.37 | 0.40 | 0.63 | 1.17 | 0.91 | 0.16 | 1.55 | 2.87 | 2.28 | 0.53 |
| *O. glumaepatula* | 1.35 | 1.73 | 1.58 | 0.13 | 0.82 | 1.20 | 1.00 | 0.12 | 2.18 | 2.81 | 2.58 | 0.22 |
| F value | | | 52.92** | | | | 8.45** | | | | 33.03** | |
| LSD 1% | | | 0.32 | | | | 0.19 | | | | 0.48 | |
| Genome complex level | | | | | | | | | | | | |
| *O. sativa* complex | 0.67 | 3.37 | 1.49 | 0.59 | 0.50 | 1.50 | 1.03 | 0.20 | 1.30 | 4.87 | 2.52 | 0.73 |
| *O. officinalis* complex | 0.92 | 4.23 | 2.17 | 0.68 | 0.55 | 1.80 | 1.01 | 0.23 | 1.52 | 5.56 | 3.18 | 0.83 |
| *O. meyeriana* complex | 1.82 | 3.96 | 3.25 | 0.51 | 1.08 | 1.70 | 1.31 | 0.16 | 3.14 | 5.19 | 4.56 | 0.52 |
| *O. ridleyi* complex | 2.92 | 4.30 | 3.48 | 0.48 | 0.72 | 1.08 | 0.91 | 0.11 | 3.85 | 5.20 | 4.39 | 0.44 |
| *O. coarctata* | 2.31 | 2.73 | 2.60 | 0.17 | 1.45 | 1.64 | 1.54 | 0.07 | 3.94 | 4.25 | 4.14 | 0.12 |
| F value | | | 57.60** | | | | 15.79** | | | | 44.68** | |
| LSD 1% | | | 0.82 | | | | 0.28 | | | | 0.99 | |

Example 2. Development of IR58025B Maintainer Line with Long Stigma

Crosses were made between maintainer line IR58025B and *O. longistaminata* (acc. no. 110404) to transfer long stigma traits into IR58025B background. In $BC_1F_1$, 475 $BC_1F_1$ plants from 12 crosses were evaluated for stigma length, and lines having 50% more stigma length than the recurrent parent were selected and backcrossed to produce 46 $BC_2F_1$ crossed seeds. In $BC_2F_1$, 1653 $BC_2F_1$ plants from 46 crosses were evaluated and backcrosses were made with respective recurrent parents to produce 34 $BC_3F_1$ seeds. In $BC_1F_2$, 944 plants were evaluated and 45 plants with longer stigma were selected. In $BC_2F_2$, 1109 plants were evaluated, and 98 plants with longer stigma were selected. The stigma length in different backcross generations ranged from 0.85 to 2.88 mm whereas stigma+style length ranged from 2.22-4.57 mm (Table 2).

Example 3. Development of IR68897B Maintainer Line with Long Stigma

Crosses were made between maintainer line IR68897B and *O. longistaminata* (acc. no. 110404) to transfer long stigma traits into IR68897B background. Fifteen $F_1$ plants were used to produce 364 $BC_1F_1$ plants and were evaluated for stigma length. From these, 29 plants were selected having 50% more stigma length than the recurrent parent and further backcrossed to produce $BC_2F_1$ seeds. Furthermore, 825 $BC_2F_1$ plants were evaluated and 43 plants having long stigma were backcrossed to produce $BC_3F_1$ plants. In $BC_2F_2$, 1609 plants were evaluated, and 109 plants with longer stigma were selected. The stigma length in different backcross generations ranged from 1.06 to 3.00 mm whereas stigma+style length ranged from 2.02-4.51 mm (Table 2). Seventy seven $BC_3F_1$ crosses of IR58025B and IR68897B have been produced. Stigma exertion in IR68897B, IR68897B improved lines, and IR68897A test cross progenies is presented in FIG. 11.

TABLE 2

Stigma characteristics of parents and different backcross progenies in IR58025B and IR68897B backgrounds.

| Sl. No | Generation | No. of crosses | stigma length (mm) | stigma + style length (mm) | No of crosses | stigma length (mm) | stigma + style length (mm) |
|---|---|---|---|---|---|---|---|
| 1 | IR64 | — | 1.13 | 2.26 | — | — | — |
| 2 | IR58025B | — | 1.12 | 2.36 | — | — | — |
| 3 | IR68897B | — | 1.29 | 2.56 | — | — | — |
| 4 | *O. longistaminata* | — | 2.74 | 4.06 | — | — | — |

TABLE 2-continued

Stigma characteristics of parents and different backcross progenies in IR58025B and IR68897B backgrounds.

| Sl. No | Generation | No. of crosses | stigma length (mm) | stigma + style length (mm) | No of crosses | stigma length (mm) | stigma + style length (mm) |
|---|---|---|---|---|---|---|---|
| | | | IR58025B | | | IR68897B | |
| 5 | $F_1$ | 26 | 1.86-2.74 | 2.81-4.25 | 35 | 1.35-2.92 | 2.51-4.44 |
| 6 | $BC_1F_1$ | 12 | 1.52-2.88 | 3.17-4.28 | 15 | 1.74-2.72 | 2.92-4.12 |
| 7 | $BC_2F_1$ | 46 | 0.85-2.80 | 2.22-4.57 | 29 | 1.06-3.00 | 2.0-4.51 |
| 8 | $BC_3F_1$ | 34 | — | — | 43 | — | — |

Example 4. Development of Male Sterile Lines of IR58025A and IR68897A

Forty-five backcross progenies of the cross between IR58025B and *O. longistaminata* in $BC_1F_2$ and 36 backcross progenies in $BC_2F_2$ generations with longer stigma were testcrossed with IR58025A. Among IR68897B backcross progenies, 38 plants in $BC_1F_2$ and 33 plants in $BC_2F_2$ generations derived from the cross between IR68897B and *O. longistaminata* with longer stigma were testcrossed with IR68897A. A stable maintainer line with longer stigma was developed. Simultaneously, longer and wider stigma traits were introgressed into respective CMS lines.

Example 5: Development of IR127841B Maintainer Line with Long Stigma

According to Example 4 and FIG. 1.

Example 6: Development of IR127841A Male Sterile Line with Long Stigma

According to Example 4 and FIG. 1.

Example 7: Outcrossing Rates and Hybrid Seed Quality

We obtained agro-morphological traits of the new cytoplasmic male sterile lines (CMS), IR127841A and IR127842A lines (both the lines are from the same B line) with long stigma (produced as described in Examples 5 and 6, above) and compared with the normal CMS line, IR68897A. It was observed that major agro-morphological traits of the converted CMS lines were similar to that of the normal CMS lines specifically plant height, tiller number, panicle exertion and panicle length suggesting an efficient recovery of the normal CMS line phenotype. The out-crossing rate in the new CMS line showed a significant increase over the normal CMS line. The out-crossing rate was increased from 230%-250% compared to the normal CMS line (Table 3).

TABLE 3

Agro-morphological traits, out-crossing rate and hybrid seed production in converted CMS line

| CMS lines | Plant Height (cm) | Tiller Number (No.) | Panicle Exertion (cm) | Panicle Length (cm) | Filled Grains (No.) | Unfilled Grains (No.) | Out-crossing Rate (%) |
|---|---|---|---|---|---|---|---|
| IR127841 A | 72.77 | 16.3 | −8.62 | 23.75 | 131* | 72 | 64.60-67.08 |
| IR127842 A | 75.6 | 13.7 | −7.22 | 22.9 | 131* | 60 | 67.20-76.76 |
| IR68897A | 73.97 | 16.65 | −8 | 23.95 | 33 | 86 | 27.68-30.31 |

*significant at $p < 0.05$

We carried out grain quality analysis of the new hybrid (IR127844H) from the cross between IR127841A (OCF15-107-1-9A) and IR71604-4-1-4-4-4-2-2-2-R as well as Mestizo 7 hybrid. Interestingly the new hybrid showed similar grain qualities of amylose content (24%) and gel consistency type compared with Mestizo 7 hybrid suggesting softer and flaky cooked rice characteristics. However, the new hybrid showed intermediate gelatinization temperature (GT) compared to low GT of Mestizo 7 suggesting better quality rice (Table 4).

TABLE 4

Comparative grain quality characteristics of the new hybrid

| Hybrid and Restorer line | Amylose Content (%) | Gelatinization Temperature (AlkD) | Gel Consistency |
|---|---|---|---|
| IR71604-4-1-4-4-4-2-2-2R | 22 | I | 50 |
| IR127844H* (New hybrid) | 24 | I | 45 |
| Mestizo7 (Normal hybrid) | 24 | L | 58 |

*IR127844H: IR127841A (Converted CMS line) x IR71604-4-1-4-4-4-2-2-2R

Example 8. Experiments on Out-Crossing Rate and Seed Production with Converted CMS Lines Two CMS lines, IR58025A and IR68897A converted with long and wide stigma inherited from *O. longistaminata* and produced according to Example 4 were planted in two replications with 18 plants each along with the normal CMS lines. The converted and normal CMS line plants were surrounded by IR71604-4-1-4-4-4-2-2-2R as restorer pollinator (FIG. 2). The CMS line plants had synchronized flowering with the pollinator. Data on duration of flowering, duration of glume opening, panicle exertion, pollen sterility, stigma length, stigma width and stigma viability were studied. 25 days after pollination, panicles of individual CMS line plants were harvested and percent seed set were recorded. Results showed higher rate of seed set in the range of 63.5-80.5%. Control CMS lines showed low rate of seed set in the range of 5-20% (FIGS. 5-8).

Example 9. Molecular Mapping of QTLs Influencing Floral Traits in IR64/O. Longistaminata $BC_2F_2$ Mapping Population A single plant of O. longistaminata (acc. no. 110404) was crossed with the high yielding elite cultivar IR64 to produce $F_1$ seeds. The $F_1$ plants, whose hybrid nature was confirmed through morphological and molecular markers, were used as the female parent and backcrossed to IR64 to produce 267 $BC_1F_1$ seeds. Based on their phenotypic similarity to IR64, $BC_1F_1$ plants were selected and used as the female progenitor and backcrossed to IR64 to produce 220 $BC_2F_1$ plants. A set of three hundred fifty seven (357) $BC_2F_2$ seeds from the best plants of 37 $BC_2F_1$ plants were collected for mapping of floral traits. The experiment was conducted in completely randomized block design with two replications, and ~25,000 florets from 4200 plants were dissected to collect data on stigma length, style length, stigma breadth, stigma area and total length (stigma+style) during dry season 2012 at International Rice Research Institute, Los Baños, Philippines. The mean performance of parents and minimum and maximum trait values of the population indicated transgressive segregation in the direction of cultivated parents for all traits. Most of the traits were normally distributed and skewed towards cultivated rice. Parental polymorphism survey was conducted with 822 SSR and STS markers, and 147 markers found to be polymorphic between IR64 and O. longistaminata. A linkage map was developed with 147 polymorphic markers. A total of 15 QTLs were identified by composite interval mapping for five floral traits including stigma length (6), style length (3), stigma breadth (2), stigma area (1), and total pistil length (3) (Table 5).

A major QTL i.e., qSTGL8.0 on chromosome 8 was identified at marker interval RM7356 and RM5353 for stigma length with a LOD value of 33.0 explaining 25% of total phenotypic variation. A QTL for style length (qSTYL1-1) was identified at the same marker interval, i.e., RM319 and RM3640, on chromosome 1 with a LOD value of 9.97 explaining 16% of phenotypic variation. A major QTL i.e., qSTGB1-1 was identified for stigma breadth on chromosome 1 explaining 21% of phenotypic variation with a LOD value of 14.71. For pistil length, a genomic region qPSTL11-1 on chromosome 11 was identified with a LOD value of 5.63 explaining 27% of phenotypic variation.

TABLE 5

List of floral trait QTLs detected in IR64 × O. longistaminata $BC_2F_2$ mapping population by primary mapping

| | | | Composite Interval Mapping | | | | |
|---|---|---|---|---|---|---|---|
| Sl. No. | QTL | Chr | $M_1$ | $M_2$ | LOD | A | D | $R^2$ |
| 1 | qSTGL2-1 | 2 | RM110 | S02026 | 4.6 | 0.0 | 0.2 | 0.09 |
| 2 | qSTGL5-1 | 5 | RM421 | RM7653 | 5.6 | 0.0 | 0.0 | 0.06 |
| 3 | qSTGL8-1 | 8 | RM7356 | RM5353 | 33.0 | −0.1 | 0.1 | 0.25 |
| 4 | qSTGL8-2 | 8 | RM256 | RM80 | 9.5 | −0.1 | 0.1 | 0.10 |
| 5 | qSTGL11-1 | 11 | RM590 | RM286 | 7.4 | 0.0 | 0.1 | 0.04 |
| 6 | qSTGL11-2 | 11 | RM120 | RM229 | 5.7 | −0.1 | −0.1 | 0.7 |
| 7 | qSTYL1-1 | 1 | RM319 | RM3640 | 9.97 | 0.10 | 0.00 | 0.16 |
| 8 | qSTYL5-2 | 5 | RM7653 | RM6360 | 6.12 | −0.08 | 0.01 | 0.10 |
| 9 | qSTYL8-1 | 8 | RM404 | RM1109 | 4.58 | 0.06 | −0.06 | 0.17 |
| 10 | qSTGB1-1 | 1 | RM403 | RM319 | 14.71 | −0.04 | 0.00 | 0.21 |
| 11 | qSTGB3-1 | 3 | RM3525 | RM520 | 9.77 | 0.04 | 0.01 | 0.09 |
| 12 | qSTGA8-2 | 8 | RM80 | RM502 | 8.52 | 0.04 | 0.03 | 0.03 |
| 13 | qPSTL1-1 | 1 | RM3604 | RM3746 | 8.06 | −0.13 | −0.02 | 0.08 |
| 14 | qPSTL1-3 | 1 | RM3640 | RM8134 | 8.59 | 0.15 | 0.05 | 0.09 |
| 15 | qPSTL11-1 | 11 | RM5997 | RM254 | 5.63 | 0.25 | −0.12 | 0.27 |

Example 11. QTL Fine Mapping

Six putative QTLs were detected by composite interval mapping of the genomic region conferring long exerted stigma trait (Table 6).

TABLE 6

List of QTLs detected by primary mapping of IR64 × O. longistaminata $BC_2F_2$ mapping population through composite interval mapping

| Sl. No. | *Trait Name | Chromosome | Left Marker | Right Marker | LOD | PVE (%) | **Add | **Dom |
|---|---|---|---|---|---|---|---|---|
| 1 | STGL | 2 | RM110 | SO2026 | 4.6 | 9.0 | 0.0 | 0.2 |
| 2 | STGL | 5 | RM421 | RM7653 | 5.6 | 3.0 | 0.0 | 0.0 |
| 3 | STGL | 8 | RM7356 | RM5353 | 33.0 | 25.0 | −0.1 | 0.1 |
| 4 | STGL | 8 | RM256 | RM80 | 9.4 | 10.5 | −0.1 | 0.1 |

TABLE 6-continued

List of QTLs detected by primary mapping of IR64 × O. longistaminata
BC$_2$F$_2$ mapping population through composite interval mapping

| Sl. No. | *Trait Name | Chromosome | Left Marker | Right Marker | LOD | PVE (%) | **Add | **Dom |
|---|---|---|---|---|---|---|---|---|
| 5 | STGL | 11 | RM590 | RM286 | 7.4 | 4.0 | 0.0 | 0.1 |
| 6 | STGL | 11 | RM120 | RM229 | 5.7 | 7.0 | −0.1 | −0.1 |

Among them, the QTL locus, qSTGL8.0 was found to be a major QTL with LOD as high as 33.0 and 25% R$^2$ was detected between the markers RM7356 and RM 5353 followed by minor QTL RM256 and RM80 with LOD 9.4 and 10.5% R$^2$ from the 357 BCF mapping population on the long arm of chromosome 8 within 381.82 cM to 396.18 cM of these markers (Figures. 9A and 9B).

The QTL locus, qSTGL8.0 was fine mapped to narrow down the genetic distance between the marker and the QTL to attain high co-segregation of the markers. Therefore, we used the high quality whole genome sequence information of *Oryza longistaminata* of 60,198 scaffolds assembled from 52.5× coverage Illumina HiSeq reads by SOAPdenovo ver. 2.2 and the total sequence length of 326,442,508 bp, new InDel markers specific to *O. longistaminata* were designed. Although, a major QTL detected in the region between RM7356 and RM 5353 with the marker positions between 381.82 cM and 396.18 cM respectively, we also considered the minor QTLs which were expressed from RM1109 to RM256 with the marker positions 362.34 cM and 400.04 cM respectively for fine mapping. High quality whole genome sequence of *O. longistaminata* was aligned to Nipponbare reference genome sequence for identification of insertion deletion sequences to develop InDel markers. We developed 21 new InDel markers from RM1109 to RM256 that covered the major and minor QTLs as well. These 21 InDel markers were designed with a minimum interval of 37 kb to a maximum interval of 655 kb. Of the 21 InDel markers, 14 markers showed polymorphism between IR64 and *O. longistaminata*, 357 BC$_2$F$_2$ plants which were used previously for the primary mapping were again genotyped by using these newly developed polymorphic InDel markers and subjected to QTL analysis for fine mapping. Further QTL analysis revealed that, there were two sub QTLs: qSTGL8.1 and qSTGL8.2 which were physically positioned between PA08-03 and RM7356, and PA08-17 and PA08-18 with the sizes of 294 kb and 171 kb respectively. These markers were found associated with long stigma exertion trait transferred from *O. longistaminata*. We identified 78 recombinants for both the flanking markers, PA08-03 and RM7356 of qSTGL8.1 and 64 and 76 recombinants for the flanking markers, PA08-17 and PA08-18 of qSTGL8.2 respectively. The QTL locus, qSTGL8.0 was narrowed down from approximately 3.89 Mb to 294 kb (qSTGL8.1) and 171 kb (qSTGL8.2) to achieve significant high marker-trait association (FIGS. 9C and 9D, 9E). Of the two fine mapped QTLs, the qSTGL8.2 locus has high LOD (24.0) and R$^2$ (14%) compared to the qSTGL8.1 (Table 7) indicating the chances of more contribution to long exerted stigma expression.

TABLE 7

List of QTLs detected by fine mapping of IR64 × O. longistaminata
BC$_2$F$_2$ mapping population through composite interval mapping

| Sl. No. | *Trait Name | Chromosome | Position | Left Marker | Right Marker | LOD | PVE (%) | **Add | **Dom |
|---|---|---|---|---|---|---|---|---|---|
| 1 | STGL | 8 | 283 | PA08-03 | RM7356 | 19.0 | 12.0 | 0.0 | 0.2 |
| 2 | STGL | 8 | 337 | PA08-17 | PA08-18 | 24.0 | 14.0 | −0.1 | 0.0 |

*STGL: Stigma length
**Add: Additive effect;
**Dom: Dominance effect

Example 12. Marker Validation for the Long Exerted Stigma

135 BC$_2$F$_3$ plants were used for the marker validation studies. Genotype data of primary mapped flanking markers (SSRs) and fine mapped markers (InDels) and phenotype data (stigma length) were compared for the computation of percent marker-trait co-segregation (FIG. 9F and Table 8).

TABLE 8

List of newly designed O. Longistaminata-derived gene specific InDel
markers with their sequence and product sizes

| Sl. No. | Floral trait | Marker name | F primer sequence | Seq ID | R primer sequence | Seq ID | Expected Product size for Nipponbare (bp) | Expected Product size for O. longistminata (bp) |
|---|---|---|---|---|---|---|---|---|
| 1 | Stigma length (qSTGL) | RM110 | TCGAAGCCATCCACCAACGAAG | 1 | TCCGTACGCCGACGAGGTCGAG | 2 | | 211 |

TABLE 8-continued

List of newly designed O. Longistaminata-derived gene specific InDel markers with their sequence and product sizes

| Sl. No. | Floral trait | Marker name | F primer sequence | Seq ID | R primer sequence | Seq ID | Expected Product size for Nipponbare (bp) | Expected Product size for O. longistminata (bp) |
|---|---|---|---|---|---|---|---|---|
| 2 | Stigma length (qSTGL) | S02026 | TGGTCCATCATATTGCCAAC | 3 | TCCTCTCAGATCCGATTTTCA | 4 | 167 | |
| 3 | Stigma length (qSTGL) | RM421 | AGCTCAGGTGAAACATCCAC | 5 | ATCCAGAATCCATTGACCCC | 6 | 610 | |
| 4 | Stigma length (qSTGL) | RM7653 | AATTCGTCCCCGTCTCCTAC | 7 | GAATTCCAGCTCTTTGACCG | 8 | 236 | |
| 5 | Stigma length (qSTGL) | PA08-03 | GCTCTCTACATGCCCTCGTC | 9 | CCGTGTGTTGGTAGGTCAGA | 10 | 190 | 147 |
| 6 | Stigma length (qSTGL) | RM7356 | CCAAGGACACATATGCATGC | 11 | GCAATTCATGGCGCTGTTC | 12 | 224 | |
| 7 | Stigma length (qSTGL) | PA08-18 | GATCAATGTTTGGTCACCATCC | 13 | GTAGTCTCCTGCAATATCCC | 14 | 220 | 188 |
| 8 | Stigma length (qSTGL) | RM5353 | ACCCTCGATCTCCTAGGCTG | 15 | TCTACTCCAAACCCATTGCC | 16 | 226 | |
| 9 | Stigma length (qSTGL) | RM256 | GACAGGGAGTGATTGAAGGC | 17 | GTTGATTTCGCCAAGGGC | 18 | 507 | |
| 10 | Stigma length (qSTGL) | RM80 | TTGAAGGCGCTGAAGGAG | 19 | CATCAACCTCGTCTTCACCG | 20 | 349 | |
| 11 | Stigma length (qSTGL) | RM286 | GGCTTCATCTTTGGCGAC | 21 | CCGGATTCACGAGATAAACTC | 22 | 362 | |
| 12 | Stigma length (qSTGL) | RM120 | CACACAAGCCCTGTCTCACGACC | 23 | CGCTGCGTCATGAGTATGTA | 24 | 190 | |
| 13 | Stigma length (qSTGL) | RM229 | CACTCACACGAACGACTGAC | 25 | CGCAGGTTCTTGTGAAATGT | 26 | 323 | |
| 14 | Style length (qSTYL) | RM319 | ATCAAGGTACCTAGACCACCAC | 27 | TCCTGGTGCAGCTATGTCTG | 28 | 517 | |
| 15 | Style length (qSTYL) | RM6360 | GCTCGGATCAATCGAGCTC | 29 | TTTCCAGCAAGATCGACGC | 30 | 233 | |
| 16 | Style length (qSTYL) | RM404 | CCAATCATTAACCCCTGAGC | 31 | GCCTTCATGCTTCAGAAGAC | 32 | 680 | |
| 17 | Style length (qSTYL) | RM1109 | TCAAAATCACGTGTATGTAAGC | 33 | TTTACAAAGGACAGAGGGC | 34 | 224 | |
| 18 | Stigma breadth (qSTGB) | RM403 | GCTGTGCATGCAAGTTCATG | 35 | ATGGTCCTCATGTTCATGGC | 36 | 697 | |
| 19 | Stigma breadth (qSTGB) | RM319 | ATCAAGGTACCTAGACCACCAC | 37 | TCCTGGTGCAGCTATGTCTG | 38 | 517 | |

TABLE 8-continued

List of newly designed O. Longistaminata-derived gene specific InDel markers with their sequence and product sizes

| Sl. No. | Floral trait | Marker name | F primer sequence | Seq ID | R primer sequence | Seq ID | Expected Product size for Nipponbare (bp) | Expected Product size for O. longistminata (bp) |
|---|---|---|---|---|---|---|---|---|
| 20 | Stigma breadth (qSTGB) | RM3525 | ACACTCTCAGCTCATCAAGACC | 39 | GGGCAAGTGGTCAAATCTTG | 40 | | 266 |
| 21 | Stigma breadth (qSTGB) | RM520 | AGGAGCAAGAAAAGTTCCCC | 41 | GCCAATGTGTGACGCAATAG | 42 | | 710 |
| 22 | Stigma area (qSTGA) | RM502 | GCGATCGATGGCTACGAC | 43 | ACAACCCAACAAGAAGGACG | 44 | | 602 |
| 23 | Pistil length (qPSTL) | RM3604 | ATGTCAGACTCCGATCTGGG | 45 | TCTTGACCTTACCACCAGGC | 46 | | 226 |
| 24 | Pistil length (qPSTL) | RM3746 | AAATGGGCTTCCTCCTCTTC | 47 | CAGCCTTGATCGGAAGTAGC | 48 | | 234 |
| 25 | Pistil length (qPSTL) | RM3640 | TACTGGTGCAAGGATACCCC | 49 | TGCTCCAAACCTCAGTCTCC | 50 | | 228 |
| 26 | Pistil length (qPSTL) | RM8134 | AACCCTGGTTCACATTAT | 51 | AAAACAGTTAGGTCAAATTG | 52 | | 111 |
| 27 | Pistil length (qPSTL) | RM5997 | GCGACGACGAAGAAGCTAAC | 53 | CCCATCGATAGGGTTTCCTC | 54 | | 224 |
| 28 | Pistil length (qPSTL) | RM254 | AGCCCCGAATAAATCCACCT | 55 | CTGGAGGAGCATTTGGTAGC | 56 | | 560 |

McCouch-S-R, Teytelman-L, Xu-Y, Lobos-K-B, Clare-K, Walton-M, Fu-B, Maghirang-R, Li-Z, Xing-Y, Zhang-Q, Kono-I, Yano-M, Fjellstrom-R, DeClerck-G, Schneider-D, Cartinhour-S, Ware-D, Stein-L, "Development and mapping of 2240 new SSR markers for rice (Oryza sativa L.)", DNA research: an international journal for rapid publication of reports on genes and genomes, 2002, vol. 9, pp. 199-207.

The InDel marker, PA08-18 showed the highest co-segregation of 75.0% and the marker could be effectively utilized in MAS of long stigma trait introgression into hybrid parental lines toward increasing out-crossing rate (FIG. 9G).

Example 13. Background Analysis of Improved Cytoplasmic Male Sterile Lines

We used Infinium 6K SNP chip of Illumina platform to analyze the recovery of recurrent parent IR68897B genome in the newly improved CMS line, IR127841A (OCF15-107-1-9). The improved CMS line showed the highest genome recovery (80.0%) and possesses the qSTGL8.0 (a major QTL involved in long stigma exertion) (FIG. 9H).

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments disclosed herein contemplated for carrying out this invention, but that the invention will include all embodiments falling within the scope of the claims.

What is claimed is:

1. A cultivated rice plant comprising an introgression including at least one *Oryza longistaminata* dominant quantitative trait locus (QTL) associated with stigma length, the cultivated rice plant having an out-crossing rate of at least 60%, wherein said introgression is positioned on chromosome 8 and is defined by markers RM1109 and RM256, wherein RM1109 is detectable by a primer pair of SEQ ID NOs: 33 and 34 and RM256 is detectable by a primer pair of SEQ ID NOs: 17 and 18.

2. The rice plant of claim 1 being cytoplasmic male sterile line.

3. The rice plant of claim 1 being a maintainer line.

4. A hybrid rice plant having the rice plant of claim 1 as a parent, wherein the hybrid rice plant comprises said dominant QTL.

5. A processed product comprising DNA of the rice plant of claim 1, wherein the processed product comprises said dominant QTL.

6. The processed product of claim 5, being a meal.

7. A tissue culture produced from protoplasts or cells from the rice plant of claim 1, wherein the protoplasts or cells of the tissue culture are produced from a plant part selected from the group consisting of: leaves; pollen; embryos; cotyledon; hypocotyls; meristematic cells, wherein the tissue culture comprises said dominant QTL.

8. A method of producing rice meal, the method comprising:
(a) growing and collecting seeds of the hybrid rice plant of claim 4; and (b) processing said seeds to meal.

* * * * *

SEQUENCE LISTING

<160> NUMBER OF SEQ ID NOS: 56

<210> SEQ ID NO 1
<211> LENGTH: 22
<212> TYPE: DNA
<213> ORGANISM: Artificial sequence

```
<220> FEATURE:
<223> OTHER INFORMATION: Single strand DNA oligonucleotide

<400> SEQUENCE: 1
tcgaagccat ccaccaacga ag                                              22

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
tccgtacgcc gacgaggtcg ag                                              22

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
tggtccatca tattgccaac                                                 20

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
tcctctcaga tccgattttc a                                               21

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
agctcaggtg aaacatccac                                                 20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
atccagaatc cattgacccc                                                 20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
aattcgtccc cgtctcctac                                                 20
```

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
gaattccagc tctttgaccg                                              20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
gctctctaca tgccctcgtc                                              20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
ccgtgtgttg gtaggtcaga                                              20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
ccaaggacac atatgcatgc                                              20

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 12
gcaattcatg gcgctgttc                                               19

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
gatcaatgtt tggtcaccat cc                                           22

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

```
<400> SEQUENCE: 14
gtagtctcct gcaatatccc                                              20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
accctcgatc tcctaggctg                                              20

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
tctactccaa acccattgcc                                              20

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
gacagggagt gattgaaggc                                              20

<210> SEQ ID NO 18
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 18
gttgatttcg ccaagggc                                                18

<210> SEQ ID NO 19
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 19
ttgaaggcgc tgaaggag                                                18

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
catcaacctc gtcttcaccg                                              20

<210> SEQ ID NO 21
```

-continued

<210> SEQ ID NO 21
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 21
ggcttcatct ttggcgac                                                 18

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
ccggattcac gagataaact c                                             21

<210> SEQ ID NO 23
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 23
cacacaagcc ctgtctcacg acc                                           23

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
cgctgcgtca tgagtatgta                                               20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
cactcacacg aacgactgac                                               20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
cgcaggttct tgtgaaatgt                                               20

<210> SEQ ID NO 27
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
atcaaggtac ctagaccacc ac        22

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
tcctggtgca gctatgtctg        20

<210> SEQ ID NO 29
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 29
gctcggatca atcgagctc        19

<210> SEQ ID NO 30
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 30
tttccagcaa gatcgacgc        19

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
ccaatcatta acccctgagc        20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
gccttcatgc ttcagaagac        20

<210> SEQ ID NO 33
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 33
tcaaaatcac gtgtatgtaa gc        22

<210> SEQ ID NO 34
<211> LENGTH: 19
<212> TYPE: DNA

```
<213> ORGANISM: Artificial sequence
<220> FEATURE:
<223> OTHER INFORMATION: Single strand DNA oligonucleotide

<400> SEQUENCE: 34
tttacaaagg acagagggc                                                    19

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
gctgtgcatg caagttcatg                                                   20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
atggtcctca tgttcatggc                                                   20

<210> SEQ ID NO 37
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 37
atcaaggtac ctagaccacc ac                                                22

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
tcctggtgca gctatgtctg                                                   20

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
acactctcag ctcatcaaga cc                                                22

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
gggcaagtgg tcaaatcttg                                                   20
```

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
aggagcaaga aaagttcccc                                                 20

<210> SEQ ID NO 42
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 42
gccaatgtgt gacgcaatag                                                 20

<210> SEQ ID NO 43
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 43
gcgatcgatg gctacgac                                                   18

<210> SEQ ID NO 44
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 44
acaacccaac aagaaggacg                                                 20

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
atgtcagact ccgatctggg                                                 20

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 46
tcttgacctt accaccaggc                                                 20

<210> SEQ ID NO 47
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 47
aaatgggctt cctcctcttc                                                 20

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 48
cagccttgat cggaagtagc                                                 20

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
tactggtgca aggatacccc                                                 20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
tgctccaaac ctcagtctcc                                                 20

<210> SEQ ID NO 51
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 51
aaccctggtt cacattat                                                   18

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 52
aaaacagtta ggtcaaattg                                                 20

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
gcgacgacga agaagctaac                                                 20

```
<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
cccatcgata gggtttcctc                                                   20

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 55
agccccgaat aaatccacct                                                   20

<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 56
ctggaggagc atttggtagc                                                   20
```